US011712296B2

(12) United States Patent
Panescu et al.

(10) Patent No.: US 11,712,296 B2
(45) Date of Patent: *Aug. 1, 2023

(54) METHODS AND DEVICES FOR ENDOVASCULAR ABLATION OF A SPLANCHNIC NERVE

(71) Applicant: Axon Therapies, Inc., New York, NY (US)

(72) Inventors: Dorin Panescu, San Jose, CA (US); Andrew Wu, Los Altos Hills, CA (US); Zoar Jacob Engelman, New York, NY (US); Mark Gelfand, New York, NY (US); Mark S. Leung, Duncan (CA); Howard Levin, Teaneck, NJ (US)

(73) Assignee: Axon Therapies, Inc., New York, NY (US)

( * ) Notice: Subject to any disclaimer, the term of this patent is extended or adjusted under 35 U.S.C. 154(b) by 574 days.

This patent is subject to a terminal disclaimer.

(21) Appl. No.: 16/793,698

(22) Filed: Feb. 18, 2020

(65) Prior Publication Data

US 2020/0179047 A1 Jun. 11, 2020

Related U.S. Application Data

(63) Continuation of application No. 16/222,823, filed on Dec. 17, 2018, now Pat. No. 10,561,461.

(Continued)

(51) Int. Cl.
*A61B 18/14* (2006.01)
*A61B 18/00* (2006.01)
(Continued)

(52) U.S. Cl.
CPC .. *A61B 18/1492* (2013.01); *A61B 2018/0022* (2013.01); *A61B 2018/0044* (2013.01);
(Continued)

(58) Field of Classification Search
CPC ..... A61B 18/1492; A61B 18/02; A61B 18/04; A61B 18/08; A61B 18/14; A61B 18/1402;
(Continued)

(56) References Cited

U.S. PATENT DOCUMENTS 3,301,258 A 1/1967 Werner
4,403,985 A 9/1983 Boretos
(Continued)

FOREIGN PATENT DOCUMENTS

CN 1219855 A 6/1999
CN 1269708 A 10/2000
(Continued)

OTHER PUBLICATIONS

Norman: Posterior Mediastinum; As last known Jun. 6, 2013; retrieved from the internet (https:web.archive.org/web/20130606053828/ http://www.wesnorman.com/thoraxlesson5.htm); 11 pages; on Sep. 16, 2020.

(Continued)

*Primary Examiner* — Thomas A Giuliani
(74) *Attorney, Agent, or Firm* — Shay Glenn LLP; Thomas M. Zlogar

(57) ABSTRACT

Systems, devices, and methods for transvascular ablation of target tissue. The devices and methods may, in some examples, be used for splanchnic nerve ablation to increase splanchnic venous blood capacitance to treat at least one of heart failure and hypertension. For example, the devices disclosed herein may be advanced endovascularly to a target vessel in the region of a thoracic splanchnic nerve (TSN), such as a greater splanchnic nerve (GSN) or a TSN nerve root. Also disclosed are method of treating heart failure, (Continued)

such as HFpEF, by endovascularly ablating a thoracic splanchnic nerve to increase venous capacitance and reduce pulmonary blood pressure.

12 Claims, 7 Drawing Sheets

Related U.S. Application Data

(60) Provisional application No. 62/660,258, filed on Apr. 20, 2018, provisional application No. 62/599,715, filed on Dec. 17, 2017.

(51) Int. Cl.
*A61M 25/10* (2013.01)
*A61B 90/00* (2016.01)

(52) U.S. Cl.
CPC .............. *A61B 2018/00404* (2013.01); *A61B 2018/00434* (2013.01); *A61B 2018/00577* (2013.01); *A61B 2018/00791* (2013.01); *A61B 2018/00821* (2013.01); *A61B 2018/00839* (2013.01); *A61B 2018/00904* (2013.01); *A61B 2018/1472* (2013.01); *A61B 2090/392* (2016.02); *A61M 2025/1004* (2013.01)

(58) Field of Classification Search
CPC .. A61B 2018/00839; A61B 2018/0212; A61B 2018/0022; A61B 2018/00404; A61B 2018/00434; A61B 2018/0044; A61B 2018/00577; A61B 2018/1472; A61B 2018/00375; A61M 2025/1004
USPC ........ 606/20, 21, 27, 28, 41; 607/96, 98, 99, 607/101, 102, 104, 105, 113, 115, 116, 607/122
See application file for complete search history.

(56) References Cited

U.S. PATENT DOCUMENTS

| | | |
|---|---|---|
| 4,862,891 A | 9/1989 | Smith |
| 5,447,529 A | 9/1995 | Marchlinski et al. |
| 5,454,840 A | 10/1995 | Krakovsky |
| 5,458,626 A | 10/1995 | Krause |
| 5,462,545 A | 10/1995 | Wang et al. |
| 5,569,198 A | 10/1996 | Racchini |
| 5,649,974 A | 7/1997 | Nelson et al. |
| 5,658,282 A | 8/1997 | Daw et al. |
| 5,704,908 A | 1/1998 | Hofmann et al. |
| 5,722,403 A | 3/1998 | McGee et al. |
| 5,740,808 A | 4/1998 | Panescu et al. |
| 5,797,903 A | 8/1998 | Swanson et al. |
| 5,800,484 A | 9/1998 | Gough et al. |
| 5,830,213 A | 11/1998 | Panescu et al. |
| 5,836,874 A | 11/1998 | Swanson et al. |
| 5,840,076 A | 11/1998 | Swanson et al. |
| 5,846,239 A | 12/1998 | Swanson et al. |
| 5,860,974 A | 1/1999 | Abele |
| 5,868,736 A | 2/1999 | Swanson et al. |
| 5,871,483 A | 2/1999 | Jackson et al. |
| 5,891,136 A | 4/1999 | McGee et al. |
| 5,925,038 A | 7/1999 | Panescu et al. |
| 5,928,229 A | 7/1999 | Gough et al. |
| 5,961,513 A | 10/1999 | Swanson et al. |
| 6,044,846 A | 4/2000 | Edwards |
| 6,058,331 A | 5/2000 | King |
| 6,071,278 A | 6/2000 | Panescu et al. |
| 6,099,526 A | 8/2000 | Whayne et al. |
| 6,123,718 A | 9/2000 | Tu et al. |
| 6,165,172 A | 12/2000 | Farley et al. |
| 6,236,886 B1 | 5/2001 | Cherepenin et al. |
| 6,395,325 B1 | 5/2002 | Hedge et al. |
| 6,409,722 B1 | 6/2002 | Hoey et al. |
| 6,425,877 B1 | 7/2002 | Edwards |
| 6,454,766 B1 | 9/2002 | Swanson et al. |
| 6,475,213 B1 | 11/2002 | Whayne et al. |
| 6,569,160 B1 | 5/2003 | Goldin et al. |
| 6,638,275 B1 | 10/2003 | McGaffigan et al. |
| 6,656,174 B1 | 12/2003 | Hegde et al. |
| 6,658,279 B2 | 12/2003 | Swanson et al. |
| 6,658,929 B2 | 12/2003 | Atkinson |
| 6,668,198 B2 | 12/2003 | Swanson et al. |
| 6,743,197 B1 | 6/2004 | Edwards |
| 6,760,616 B2 | 7/2004 | Hoey et al. |
| 6,832,114 B1 | 12/2004 | Whitehurst et al. |
| 6,849,073 B2 | 2/2005 | Hoey et al. |
| 6,885,888 B2 | 4/2005 | Rezai |
| 6,890,315 B1 | 5/2005 | Levin et al. |
| 6,954,977 B2 | 10/2005 | Maguire et al. |
| 6,984,232 B2 | 1/2006 | Vanney et al. |
| 7,054,689 B1 | 5/2006 | Whitehurst et al. |
| 7,104,989 B2 | 9/2006 | Skarda |
| 7,149,574 B2 | 12/2006 | Yun et al. |
| 7,153,301 B2 | 12/2006 | Swartz et al. |
| 7,236,822 B2 | 6/2007 | Dobak, III |
| 7,239,912 B2 | 7/2007 | Dobak, III |
| 7,282,050 B2 | 10/2007 | Starkebaum et al. |
| 7,282,051 B2 | 10/2007 | Rioux et al. |
| 7,285,199 B2 | 10/2007 | Mitsuhashi et al. |
| 7,326,208 B2 | 2/2008 | Vanney et al. |
| 7,330,762 B2 | 2/2008 | Boveja et al. |
| 7,335,377 B2 | 2/2008 | Stern et al. |
| 7,367,972 B2 | 5/2008 | Francischelli et al. |
| 7,418,292 B2 | 8/2008 | Shafer |
| 7,427,280 B2 | 9/2008 | Gerber |
| 7,449,018 B2 | 11/2008 | Kramer |
| 7,529,582 B1 | 5/2009 | DiLorenzo |
| 7,532,938 B2 | 5/2009 | Machado et al. |
| 7,551,964 B2 | 6/2009 | Dobak, III |
| 7,599,736 B2 | 10/2009 | DiLorenzo |
| 7,623,924 B2 | 11/2009 | Narciso, Jr. |
| 7,689,276 B2 | 3/2010 | Dobak |
| 7,689,277 B2 | 3/2010 | Dobak, III |
| 7,702,386 B2 | 4/2010 | Dobak et al. |
| 7,736,362 B2 | 6/2010 | Ebert et al. |
| 7,769,442 B2 | 8/2010 | Shafer |
| 7,778,703 B2 | 8/2010 | Gross et al. |
| 7,860,570 B2 | 12/2010 | Whitehurst et al. |
| 7,865,237 B2 | 1/2011 | Machado et al. |
| 7,877,146 B2 | 1/2011 | Rezai et al. |
| 7,921,657 B2 | 4/2011 | Littrup et al. |
| 7,937,145 B2 | 5/2011 | Dobak |
| 8,007,490 B2 | 8/2011 | Rioux et al. |
| 8,155,744 B2 | 4/2012 | Rezai |
| 8,241,273 B2 | 8/2012 | Whayne et al. |
| 8,270,568 B2 | 9/2012 | Pitt |
| 8,295,926 B2 * | 10/2012 | Dobak, III ............. A61K 45/06 607/3 |
| 8,321,030 B2 | 11/2012 | Maniak et al. |
| 8,399,443 B2 | 3/2013 | Seward |
| 8,401,667 B2 | 3/2013 | Gustus et al. |
| 8,414,508 B2 | 4/2013 | Thapliyal et al. |
| 8,433,412 B1 | 4/2013 | Westlund et al. |
| 8,473,051 B1 | 6/2013 | Wessels et al. |
| 8,483,835 B2 | 7/2013 | Errico et al. |
| 8,611,496 B2 | 12/2013 | Terunuma et al. |
| 8,676,326 B1 | 3/2014 | Farazi |
| 8,676,362 B2 | 3/2014 | Gabel et al. |
| 8,798,738 B2 | 8/2014 | Machado et al. |
| 8,814,793 B2 | 8/2014 | Brabrand |
| 8,911,439 B2 | 12/2014 | Mayse et al. |
| 8,994,536 B2 | 3/2015 | Margon |
| 8,998,894 B2 | 4/2015 | Mauch et al. |
| 9,005,100 B2 | 4/2015 | Gnanashanmugam et al. |
| 9,022,948 B2 | 5/2015 | Wang |
| 9,028,472 B2 | 5/2015 | Mathur et al. |
| 9,033,969 B2 | 5/2015 | Azamian et al. |
| 9,037,259 B2 | 5/2015 | Mathur |
| 9,072,902 B2 | 7/2015 | Mathur et al. |
| 9,125,661 B2 | 9/2015 | Deem |
| 9,125,668 B2 | 9/2015 | Subramaniam et al. |

(56) References Cited

U.S. PATENT DOCUMENTS

| | | | |
|---|---|---|---|
| 9,162,075 B2 | 10/2015 | Sluijter et al. |
| 9,174,050 B2 | 11/2015 | Mathur et al. |
| 9,199,091 B2 | 12/2015 | Danek et al. |
| 9,245,182 B2 | 1/2016 | Jania et al. |
| 9,278,196 B2 | 3/2016 | Fischell et al. |
| 9,345,530 B2 | 5/2016 | Ballakur et al. |
| 9,345,900 B2 | 5/2016 | Wu et al. |
| 9,370,657 B2 | 6/2016 | Tehrani et al. |
| 9,439,580 B2 | 9/2016 | Hatlestad et al. |
| 9,439,598 B2 | 9/2016 | Shimada et al. |
| 9,592,386 B2 | 3/2017 | Mathur et al. |
| 9,603,659 B2 | 3/2017 | Subramaniam et al. |
| 9,743,845 B2 | 8/2017 | Wang |
| 9,757,193 B2 | 9/2017 | Zarins et al. |
| 9,895,539 B1 | 2/2018 | Heit et al. |
| 10,207,110 B1 | 2/2019 | Gelfand et al. |
| 10,376,308 B2 * | 8/2019 | Levin ................ A61B 18/1492 |
| 10,561,461 B2 * | 2/2020 | Panescu ............ A61B 18/1492 |
| 2002/0087152 A1 | 7/2002 | Mikus et al. |
| 2002/0165532 A1 | 11/2002 | Hill et al. |
| 2002/0198520 A1 | 12/2002 | Coen et al. |
| 2003/0109869 A1 | 6/2003 | Shadduck |
| 2003/0216792 A1 | 11/2003 | Levin et al. |
| 2004/0147837 A1 | 7/2004 | Macaulay et al. |
| 2004/0147877 A1 | 7/2004 | Heuser |
| 2004/0148019 A1 | 7/2004 | Vidlund et al. |
| 2004/0247849 A1 | 12/2004 | Truckai |
| 2005/0010095 A1 | 1/2005 | Stewart et al. |
| 2005/0203462 A1 | 9/2005 | Katoh et al. |
| 2005/0245923 A1 | 11/2005 | Christopherson et al. |
| 2006/0189972 A1 | 8/2006 | Grossman |
| 2006/0200121 A1 * | 9/2006 | Mowery ............ A61B 18/1477 |
| | | 606/41 |
| 2006/0224118 A1 | 10/2006 | Morris et al. |
| 2007/0167984 A1 | 7/2007 | Kieval et al. |
| 2007/0208333 A1 | 9/2007 | Uchida et al. |
| 2007/0213704 A1 | 9/2007 | Truckai et al. |
| 2007/0224253 A1 | 9/2007 | Franklin |
| 2008/0114335 A1 | 5/2008 | Flickinger et al. |
| 2008/0125748 A1 | 5/2008 | Patel |
| 2008/0200972 A1 | 8/2008 | Rittman |
| 2009/0036794 A1 | 2/2009 | Stubhaug et al. |
| 2009/0280178 A1 | 11/2009 | Hedge et al. |
| 2010/0152731 A1 | 6/2010 | de la Rama et al. |
| 2010/0168820 A1 | 7/2010 | Maniak et al. |
| 2010/0241113 A1 | 9/2010 | Ingle |
| 2010/0249702 A1 | 9/2010 | Magana et al. |
| 2010/0286684 A1 | 11/2010 | Hata et al. |
| 2010/0305664 A1 | 12/2010 | Wingeler et al. |
| 2010/0312295 A1 | 12/2010 | Vase et al. |
| 2011/0022127 A1 | 1/2011 | Averina et al. |
| 2011/0028962 A1 | 2/2011 | Werneth et al. |
| 2011/0098761 A1 | 4/2011 | Wiltenberger et al. |
| 2011/0144639 A1 | 6/2011 | Govari |
| 2011/0224750 A1 | 9/2011 | Scheiner |
| 2011/0238083 A1 | 9/2011 | Moll et al. |
| 2011/0313417 A1 | 12/2011 | La Rama et al. |
| 2012/0065554 A1 | 3/2012 | Pikus |
| 2012/0089047 A1 | 4/2012 | Ryba et al. |
| 2012/0089123 A1 | 4/2012 | Organ et al. |
| 2012/0116354 A1 | 5/2012 | Heuser |
| 2012/0136350 A1 | 5/2012 | Goshgarian et al. |
| 2012/0143293 A1 | 6/2012 | Mauch et al. |
| 2012/0265198 A1 | 10/2012 | Crow et al. |
| 2012/0271162 A1 | 10/2012 | Liao et al. |
| 2012/0289369 A1 | 11/2012 | Fogarty |
| 2012/0296329 A1 | 11/2012 | Ng |
| 2013/0023758 A1 | 1/2013 | Fabro |
| 2013/0035682 A1 * | 2/2013 | Weil ...................... A61N 5/103 |
| | | 606/33 |
| 2013/0096550 A1 | 4/2013 | Hill |
| 2013/0103026 A1 | 4/2013 | Kleshinski et al. |
| 2013/0226201 A1 | 8/2013 | Miller et al. |
| 2013/0237948 A1 | 9/2013 | Donders et al. |
| 2013/0282990 A1 | 10/2013 | Parsonage et al. |
| 2013/0289369 A1 | 10/2013 | Margolis |
| 2013/0296646 A1 | 11/2013 | Barbut et al. |
| 2013/0304047 A1 | 11/2013 | Grunewald et al. |
| 2013/0331813 A1 | 12/2013 | Barbut et al. |
| 2014/0005706 A1 | 1/2014 | Gelfand et al. |
| 2014/0012251 A1 | 1/2014 | Himmelstein |
| 2014/0025069 A1 | 1/2014 | Willard et al. |
| 2014/0031727 A1 | 1/2014 | Wamking |
| 2014/0058294 A1 | 2/2014 | Gross et al. |
| 2014/0058376 A1 | 2/2014 | Horn et al. |
| 2014/0058377 A1 | 2/2014 | Deem et al. |
| 2014/0067003 A1 | 3/2014 | Vase et al. |
| 2014/0088585 A1 | 3/2014 | Hill et al. |
| 2014/0088588 A1 | 3/2014 | Jarrard |
| 2014/0121641 A1 | 5/2014 | Fischell et al. |
| 2014/0121644 A1 | 5/2014 | Fischell et al. |
| 2014/0180273 A1 | 6/2014 | Nair |
| 2014/0214129 A1 | 7/2014 | Waataja et al. |
| 2014/0276718 A1 | 9/2014 | Turovskiy et al. |
| 2014/0278742 A1 | 9/2014 | Nabutovsky et al. |
| 2014/0303617 A1 | 10/2014 | Shimada |
| 2015/0011834 A1 | 1/2015 | Ayala et al. |
| 2015/0105659 A1 | 4/2015 | Salahieh et al. |
| 2015/0119674 A1 | 4/2015 | Fischell et al. |
| 2015/0141810 A1 | 5/2015 | Weadock |
| 2015/0141985 A1 | 5/2015 | Mayse et al. |
| 2015/0208949 A1 | 7/2015 | Tupin et al. |
| 2015/0223877 A1 | 8/2015 | Behar et al. |
| 2015/0245867 A1 | 9/2015 | Gross |
| 2015/0335286 A1 | 11/2015 | Boydell |
| 2016/0106499 A1 | 4/2016 | Ogata et al. |
| 2016/0151112 A1 | 6/2016 | Ku et al. |
| 2016/0158554 A1 | 6/2016 | Graig |
| 2016/0163062 A1 | 6/2016 | Garber |
| 2016/0192981 A1 | 7/2016 | Dimmer et al. |
| 2016/0199127 A1 | 7/2016 | Prutchi |
| 2016/0220851 A1 | 8/2016 | Mayse et al. |
| 2016/0296171 A1 | 10/2016 | Drori et al. |
| 2016/0317621 A1 * | 11/2016 | Bright .................... A61K 47/10 |
| 2016/0354137 A1 | 12/2016 | Fischell et al. |
| 2016/0374754 A1 | 12/2016 | Asirvatham et al. |
| 2017/0035990 A1 | 2/2017 | Swift |
| 2017/0049989 A1 * | 2/2017 | Kapural ................ A61M 5/162 |
| 2017/0143945 A1 | 5/2017 | Culbert et al. |
| 2017/0202614 A1 | 7/2017 | Gross et al. |
| 2017/0216602 A1 | 8/2017 | Waataja et al. |
| 2017/0231490 A1 | 8/2017 | Toth et al. |
| 2017/0252101 A1 | 9/2017 | Hata et al. |
| 2018/0042669 A1 | 2/2018 | Curley et al. |
| 2018/0110561 A1 | 4/2018 | Levin et al. |
| 2018/0178019 A1 | 6/2018 | Reddy et al. |
| 2019/0069942 A1 | 3/2019 | Azamian et al. |
| 2019/0175912 A1 | 6/2019 | Gelfand et al. |
| 2019/0298460 A1 | 10/2019 | Al-Jadda et al. |
| 2019/0343581 A1 | 11/2019 | Panescu et al. |
| 2019/0350650 A1 * | 11/2019 | Levin ................... A61N 1/36017 |
| 2020/0179045 A1 * | 6/2020 | Levin .................... A61N 1/0551 |
| 2021/0128229 A1 * | 5/2021 | Panescu ............ A61B 18/0218 |
| 2021/0298824 A1 | 9/2021 | Iranitalab et al. |
| 2021/0393326 A1 * | 12/2021 | Levin ................ A61B 18/1492 |
| 2022/0000545 A1 * | 1/2022 | Levin ................ A61B 18/1492 |
| 2022/0039863 A1 | 2/2022 | Bapana et al. |
| 2022/0257315 A1 * | 8/2022 | Levin ................ A61B 18/1492 |
| 2022/0338924 A1 | 10/2022 | Levin et al. |

FOREIGN PATENT DOCUMENTS

| | | |
|---|---|---|
| CN | 101600471 A | 12/2009 |
| CN | 102670264 A | 9/2012 |
| CN | 103118619 A | 5/2013 |
| CN | 103220984 A | 7/2013 |
| CN | 103313671 A | 9/2013 |
| CN | 103857353 A | 6/2014 |
| CN | 103908336 A | 7/2014 |
| CN | 104066395 A | 9/2014 |
| CN | 104114220 A | 10/2014 |
| CN | 104257426 A | 1/2015 |
| CN | 104640583 A | 5/2015 |
| EP | 2662027 A1 | 11/2013 |

(56) References Cited

FOREIGN PATENT DOCUMENTS

| | | |
|---|---|---|
| EP | 2020943 B1 | 7/2015 |
| EP | 2755588 B1 | 5/2016 |
| EP | 2934357 B1 | 11/2017 |
| JP | 2003526481 A | 9/2003 |
| JP | 2008510530 A | 4/2008 |
| JP | 2009500052 A | 8/2009 |
| JP | 2012030010 A | 2/2012 |
| JP | 2015002920 A | 1/2015 |
| JP | 2015119830 A | 7/2015 |
| JP | 2015536186 A | 12/2015 |
| WO | WO99/12489 A2 | 3/1999 |
| WO | WO01/66177 A1 | 9/2001 |
| WO | WO2004/039428 A2 | 5/2004 |
| WO | WO2007/082216 A1 | 7/2007 |
| WO | WO2008/049084 A2 | 4/2008 |
| WO | WO2014/150887 A1 | 9/2014 |
| WO | WO2014/197625 A1 | 12/2014 |
| WO | WO2016/084081 A2 | 6/2016 |
| WO | WO2016/090175 A1 | 6/2016 |
| WO | WO2016/132340 A1 | 8/2016 |
| WO | WO2016/176333 A1 | 11/2016 |
| WO | WO2017/074920 A1 | 5/2017 |
| WO | WO2017/096007 A1 | 8/2017 |
| WO | WO2018/125822 A2 | 7/2018 |

OTHER PUBLICATIONS

Panescu et al.; U.S. Appl. No. 16/963,559 entitled "Methods and devices for endovascular ablation of a splanchnic nerve," filed Jul. 21, 2020.

Piciucchi et al.; The azygos vein pathway: an overview from anatomical variations of pathological changes; Insights Imaging; 5(5); pp. 619-628; Oct. 2014.

Adamopoulos et al; Comparison of different methods for assessing sympathovagal balance in chronic congestive heart failure secondary to coronary artery disease; The American Journal of Cardiology; 70(20); pp. 1576-1582; Dec. 15, 1992.

Andren-Sandberg et al.; Thoracoscopic splanchnicectomy for chronic, severe pancreatic pain; in Seminars in Laparoscopic Surgery; 3(1); Sage CA: Thousand Oaks CA; Sage Publications; pp. 25-33; Mar. 1, 1996.

Barnes et al.; Haemodynamic responses to stimulation of the splanchnic and cardiac sympathetic nerves in the anaesthelized cat; The Journal of Physiology; 378; pp. 417-436; Sep. 1986.

Bauereisen et al.; The importance of the mesenteric mechanoreceptors for the reflex innervation of resistance blood vessels capacity blood vessels in the splanchnic area; Pflugers Archiv fur die gesamte Physlologie des Menschen und der Tiere; 276; pp. 445-455; Jan. 1963.

Bradley et al.; Nerve blocks and neuroablative surgery for chronic pancreatitis; World J. Surg.; 27(11); pp. 1241-1248; Nov. 1, 2003.

Brooksby et al.; Dynamic changes in splanchnic blood flow and blood volume in dogs during activation of sympathetic nerves; Circulation Research; XXIX(3); pp. 227-238; Sep. 1971.

Brunner et al.; Carotid sinus baroreceptor control of splanchnic resistance and capacity. Am J Physiol.; 255; pp. H1305-H1310; Dec. 1988.

Burkhoff et al.; Why does pulmonary venous pressure rise after on of LV dysfunction: a theoretical analysis; Am. J. Physiol.; 265(5, pt. 2); pp. H1819-H1828; Nov. 1993.

Buscher et al.; Limited effect of thoracoscopic splanchnicectomy in the treatment of severe chronic pancreatitis pain: a prospective long-term analysis of 75 cases; Surgery; 143(6); pp. 715-722; Jun. 30, 2008.

Carneiro et al.; Change in liver blood flow and blood content in dogs during direct and reflex alteration of hepatic sympathetic nerve activity; Circulation Research; 40(2); pp. 150-158; Feb. 1, 1977.

Cody et al.; Captopril kinetics in chronic congestive heart failure; Clin pharmacol Ther.; 32(6); pp. 721-726; Dec. 1982.

Cuschieri et al.; Bilateral endoscopic splanchnicectomy through a posterior thoracoscopic approach; Journal of the Royal College of Surgeons of Edinburgh; 39(1); pp. 44-47; Feb. 1994.

Diedrich et al.; Segmental orthostatic fluid shifts; Clinical autonomic research; 14(3); pp. 146-147; Jun. 2004.

Edwards Lifesciences; ClearSight System (brochure; No. AR11578); 4 pgs.; © 2014.

Edwards; The glycogenolytic response to stimulation of the splanchnic nerves in adrenalectomized calves, sheep, dogs, cats and pigs; J Physiol.; 213; pp. 741-759; Mar. 1971.

Eisenberg et al.; Neurolytic celiac plexus block for treatment of cancer pain: A meta-analysis; Anesth Analg; 80(2); pp. 290-295; Feb. 1995.

Fallic et al., Sympathetically mediated changes in capacitance: Redistribution of the venous reservoir as a cause of decompensation; Circulation: Heart Failure; 4; pp. 669-675; Sep. 2011.

Ferrara et al; Hemodynamics of the splanchnic and systemic circulation after hypotonic water load-comparision between normal subjects and patients with congestive heart failure; Acta Cardiologica; 38(2): pp. 81-88; Dec. 1982.

Fiaccadori et al.; Ultrafiltration in Heart Failure; Am Heart J.; 161(3); pp. 439-449; Mar. 2011.

Folkow et al.; The Effect of Graded Vasoconstrictor Fibre Stimulation on the Intestinal Resistance and Capacitance Vessels; Acta physiologica Scandinavica; 61; pp. 445-457; Aug. 1964.

Foss et al.; Reversal of genetic salt-sensitive hypertension by targeted sympathetic ablation; Hypertension; 61(4); pp. 806-811; Apr. 1, 2013.

Francis et al.; Clinical notes, suggestions and new instrument; JAMA; 134(1); pp. 20-21; May 3, 1947.

Fudim et al.; Role of volume redistribution in the congestion of heart failure; Journal of the American Heart Association; 6(8); e006817; 11 pages; Aug. 1, 2017.

Fujita; Splanchnic circulation following coeliac plexus block; Acta Anaesthesiol Scand.; 32(4); pp. 323-327; May 1988.

Gambro®; Aquadex FlexFlowTM (brochure, No. L5189 Rev. B); 4 pgs.; © 2011 (August).

Garcea et al.; Percutaneous splanchnic nerve radiofrequency ablation for chronic abdominal pain; ANZ Journal of Surgery; 75(8); pp. 640-644; Aug. 1, 2005.

Giraudo et al.; Endoscopic palliative treatment of advanced pancreatic cancer: Thoracoscopic splanchnicectomy and laparoscopic gastrojunostomy; Annals of Oncology; 10(4); pp. S278-S280; Jan. 1, 1999.

Goldblatt et al.; Studies on experimental hypertension II: The effect of resection of splanchnic nerves on experimental renal hypertension; The Journal of Experimental Medicine; 65(2); pp. 233-241; Feb. 1, 1937.

Goroszeniuk et al.; Permanent percutaneous splanchnic nerve neuromodulation for management of pain due to chronic pancreatitis: A case report; Neuromodulation; :14(3); pp. 253-257; May-Jun. 2011.

Greenway et al.; Role of splanchnic venous system in overall cardiovascular homeostasis; In Federal Proceedings; 42(6); pp. 1678-1684; Apr. 1983.

Greenway; Blockade of reflex venous capacitance responses in liver and spleen by hexamethonium, atropine, and surgical section; Can. J. Physiol. Pharmacol.; 69(9); 1284-1287; Sep. 1991.

Griffith et al.; The vasomotor control of the liver circulation; American Journal of Physiology; 95(1); pp. 20-34; Oct. 1930.

Griffith et al.; Vasomotor Control of the Liver Circulation. Proceedings of the Society for Experimental Biology and Medicine; 27(7); pp. 673-674; Apr. 1930.

Herman et al.; Splenic afferents and some of their reflex responses; American Journal of Physiology—Regulatory, Integrative and Comparative Physiology; 242(3); pp. R247-R254; Mar. 1982.

Ihse et al.; Bilateral thoracoscopic splanchnicectomy: effects on pancreatic pain and function; Annals of Surgery; 230(6); pp. 785-791; Dec. 1, 1999.

Ischia et al; A new approach to the neurolytic block of the coeliac plexus: the transaortic technique; Pain; 16(4); pp. 333-341; Aug. 31, 1983.

(56) References Cited

OTHER PUBLICATIONS

Johnson et al.; An open randomized comparison of clinical effectiveness of protocol-driven opiod analgesia, celiac plexus block or thoracoscopic splanchnicectomy for pain mangement in patients with pancreatic and other abdominal malignancies; Pancreatology; 9(6); pp. 755-763; Jan. 1, 2009.
Kang et al.; Bilateral thoracoscopic splanchnicectomy with sympathectomy for managing abdominal pain in cancer patients; Am J Surg; 194(1); pp. 23-29; Jul. 2007.
Katri et al.; Thoracoscopic splanchnicectomy for pain control in irresectable pancreatic cancer; Journal of Laparoendoscopic and Advanced Surgical Techniques; 18(2); pp. 199-203; Apr. 1, 2008.
Kaufman et al.; Effect of portal hypertensionon splenic blood flow, Intrasplenic extravasation and systemic blood pressure; American Journal of Physiology—Regulatory, Integrative and Comparative Physiology; 284(6); pp. R1580-R1585; Jun. 1, 2003.
Kimura et al.; Application of electrical impedance analysis for diagnosis of a pulmonary mass; Chest; 105(6); pp. 1679-1682; Jun. 1994.
King et al.; Splanchnic circulation is a critical neural target in angiotensin II salt hypertension in rats; Hypertension; 50(3); pp. 547-556; Sep. 2007.
Krishna et al.; Video-assisted thoracoscopic sympathectomy-splanchnicectomy for pancreatic cancer pain; Journal of Pain and Symptom Management; 22(1); pp. 610-616; Jul. 1, 2001.
Lang-Lazdunski et al.; Videothoracoscopic splanchnicectomy for intractable pain from adrenal metastasis; Ann Thorac Surg; 73(4); pp. 1290-1292; Apr. 2002.
Le Pimpec Barthes; Thoracoscopic splanchnicectomy for control of intractable pain in pancreatic cancer; The Annals of Thoracic Surgery; 65(3); pp. 810-813; Mar. 31, 1998.
Leksowski; Thoracoscopic splanchnicectomy for the relief of pain due to chronic pancreatitis; Surg Endosc.; 15(6); pp. 592-596; Jun. 2001.
Lica et al.; Thoracoscopic left splanchnicectomy—role in pain control in unresectable pancreatic cancer. Initial experience: Chirurgia; 109(3); pp. 313-317; May-Jun. 2014.
Lieberman et al.; Celiac plexus neurolysis with the modified transaortic approach; Radiology; 175(1); pp. 274-276; Apr. 1990.
Lillemoe et al; Chemical splanchnicectomy in patients with unresectable pancreatic cancer. A prospective randomized trial; Annals of Surgery; 217(5): pp. 447-457; May 1, 1993.
Lin et al.; Bilateral thoracoscopic lower sympathetic-splanchnicectomy for upper abdominal cancer pain. The European journal of surgery; Supplement 572; pp. 59-62; 1994.
Lonroth et al.; Unilateral left-side thoracoscopic sympathectomy for visceral pain control: a pilot study; The European Journal of Surgery; 163(2); pp. 97-100; Feb. 1, 1997.
Maass-Moreno et al.; Carotid baroreceptor control of liver and spleen volume in cats; Am J Physiol; 260(1 Pt 2); pp. H254-H259; Jan. 1991.
Maher et al.; Thoracoscopic splanchnicectomy for chronic pancreatitis pain; Surgery; 120(4); pp. 603-610; Oct. 1996.
Myhre et al.; Monitoring of celiac plexus block in chronic pancreatitis; Pain; 38(3); pp. 269-274; Sep. 1989.
Nakazato et al; Extrinsic innervation of the canine abdominal vena cava and the origin of cholinergic vasoconstrictor nerves; J. Physiol.; 328; pp. 191-203; Jul. 1982.
Nath et al.; Biophysics and pathology of catheter energy delivery systems; Progress in Cardiovascular Diseases; XXXVII(4); pp. 185-204; Jan./Feb. 1995.
Pan et al.; Differential responses of regional sympathetic activity and blood flow to visceral afferent stimulation; Am J Physiol Regul Integr Comp Physiol.; 280(6); pp. R1781-R1789; Jun. 2001.
Pietrabissa et al.; Thoracoscopic splanchnicectomy for pain relief in unresectable pancreatic cancer; Archives of Surgery; 135(5); pp. 332-335; Mar. 1, 2000.
Plancarte et al.; Management of chronic upper abdominal pain in cancer: transdiscal blockage of the splanchnic nerves; Regional Anesthesia and Pain Medicine; 35(6); pp. 500-506; Nov. 1, 2010.

Prasad et al.; Thoracoscopic splanchinicectomy as a pallative procedure for pain relief in carcinoma pancreas; Journal of Minimal Access Surgery; 5(2); pp. 37-39; (Author Manuscript); Apr. 1, 2009.
Raj; Celiac plexus/splanchnic nerve blocks; Techniques in Regional Anesthesia and Pain Management; 5(3); pp. 102-115; Jul. 2001.
Raj et al.; Radiofrequency lesioning of splanchnic nerves; Pain Practice; 2(3); pp. 242-247; Sep. 2002.
Saenz et al.; Thoracoscopic splanchicectomy for pain control in patients with unresectable carcinoma of the pancreas; Surgical Endoscopy; 14(8); pp. 717-720; Aug. 1, 2000.
Sastre et al.; Transhiatal bilateral splanchnicotomy for pain control in pancreatic cancer: basic anatomy, surgical technique, and immediate results in fifty-one cases; Surgery; 111(6); pp. 640-646; Jun. 1992.
Scott-Douglas et al.; Effects of acute volume loading and hemorrhage on intestinal vascular capacitance: a mechanism whereby capacitance modulates cardiac output; Can. J. Cardiol.; 18(5); pp. 515-522; May 5, 2002.
Shimada et al.; Clinical evaluation of transhiatal bilateral splanchnicotomy for patients with intractable supramesenteric pain; Surgery Today; 29(11); pp. 1136-1140; Nov. 1999.
Smigielski et al.; Assessment of quality of life in patients with non-operated pancreatic cancer after videothoracoscopic splanchnicectomy; Videosurgery and Other Miniinvasive Techniques; 6(3); pp. 132-137; Sep. 1, 2011.
Stefaniak et al.; A comparison of two invasive techniques in the management of intractable pain due to inoperable pancreatic cancer; European Journal of Surgical Oncology; 31(7); pp. 768-773; Sep. 30, 2005.
Takahashi et al.; Thoracoscopic splanchnicectomy for the relief of intractable pain; Surgical Endoscopy; 10(1); pp. 65-68; Jan. 1, 1996.
Tavassoli et al.; Thoracoscopic splanchnicectomy for pain control in urresectable pancreatic cancer; Journal of Cardio-Thoracic Medicine; 1(2): pp. 53-56; Aug. 6, 2013.
Tsybenko et al.; Central nervous control of hapatic circulation; J Aut Nerv Sys; 33(3); pp. 255-266; May 1991.
Van Vliet et al.; Time course of renal responses to greater splanchnic nerve stimulation; American Journal of Physiology Regulatory, Integrative and Comparative Physiology; 260(5); pp. R894-R905; May 1991.
Verhaegh et al.; Percutaneous radiofrequency ablation of the splanchnic nerves with the chronic pancreatitis: results of single and repeated procedures in 11 patients; Pain Practice; 13(8); pp. 621-626; (Author Manuscript): Nov. 1, 2013.
Wilkins et al.; The effect of splanchnic sympathectomy in hypertensive patients upon estimated hepatic blood flow in the upright as contrasted with the horizontal position; Journal of Clinical Investigation; 30(3); pp. 312-317; Mar. 1951.
Worsey et al.; Thoracoscopic pancreatic denervation for pain control in irrsectable pancreatic cancer; British Journal of Surgery; 80(8); pp. 1051-1052; Aug. 1, 1993.
Yan et al.; Neurolytic celiac plexus block for pain control in unresectable pancreatic cancer; Am J Gastroenterol; 102(2); pp. 430-438; Feb. 2007.
Levin et al.; U.S. Appl. No. 15/017,260 entitled "Devices And Methods For Treatment Of Heart Failure By Splanchnic Nerve Ablation," filed Feb. 5, 2016.
Levin et al.; U.S. Appl. No. 16/318,447 entitled "Devices, systems, and methods for treatment of heart failure by splanchnic nerve ablation," filed Jan. 17, 2019.
Raj et al.; The development of a technique for radiofrequency lesioning of splanchnic nerves; Current Review of Pain; 3(5); pp. 377-387; Oct. 1999.
Levin et al.; U.S. Appl. No. 17/452,305 entitled "Devices, systems, and methods for treatment of heart failure by splanchnic nerve ablation," filed Oct. 26, 2021.
Gelfand et al.; U.S. Appl. No. 17/644,998 entitled "Methods, systems and devicesfor endovascular electroporation of a greater splanchnic nerve," filed Dec. 17, 2021.
Baghdadi et al.; Systemic review of the role of thoracoscopic splanchnicectomy in palliating the pain of patients with chronic pancreatitis; Surgical endoscopy; 22(3); pp. 580-588; Dec. 28, 2007.

(56) References Cited

OTHER PUBLICATIONS

Buscher et al.; Bilateral thoracoscopic splanchnicectomy for pain in patients with chronic pancreatitis impairs adrenomedullary but not noradrenergic sympathetic function; Surgical Endoscopy; 26(8); p. 2183-2188; Aug. 2012.

Chatterjee et al.; Novel interventional therapies to modulate the autonomic tone in heart failure; JACC: Heart Failure; 3(10); pp. 786-802; Oct. 2015.

Crespy et al.; Anatomical bases of the transhiatus approach to the greater splanchnic nerve; Anatomia Clinica; 6(4); pp. 247-254; Dec. 1, 1984.

Dayal et al.; Variations in the formation of thoracic splanchnic nerves; European Journal of Anatomy; vol. 18; pp. 141-151; (year of pub. sufficiently earlier than effective US filing date and any foreign priority date) 2014.

Del Rio et al.; Carotid chemoreceptor ablation improves survival in heart failure: rescuing autonomic control of cardiorespiratory function; Journal of the American College of Cardiology; 62(25); pp. 2422-2430; Dec. 24, 2013.

Gafanovich et al.; Chronic diarrhea-induced by celiac plexus block?; Journal of Clinical Gastroenterology; 26(4); pp. 300-302; Jun. 1, 1998.

Girouard et al.; Optical mapping in a new guinea pig model of ventricular tachycardia reveals mechanisms for multiple wavelengths in a single reentrant circuit; Circulation; 93(3); pp. 603-613; Feb. 1, 1996.

Loukas et al.; A review of the thoracic splanchnic nerves and celiac ganglia; Clinical Anatomy; 23(5); pp. 512-522; Jul. 2010.

Mallet-Guy et al.; Treatment of chronic pancreatitis by unilateral splanchnicectomy; Archives of Surgery; 60(2); pp. 233-241; Feb. 1, 1950.

Masuda et al.; Splanchnicectomy for pancreatic cancer pain; BioMed Research International; Jan. 1, 2014.

Naidoo et al.; Thoracic splanchnic nerves: implications for splanchnic denervation; Journal of Anatomy; 199(5); pp. 585-590; Nov. 2001.

Sadar et al.; Bilateral thoracic sympathectomy-splanchnicectomy in the treatment of intractable pain due to pancreatic carcinoma; Cleveland Clinic Quarterly; 41; pp. 185-188; (year of pub. sufficiently earlier than effective US filing date and any foreign priority date)1974.

Triposkiadis et al.; The sympathetic nervous system in heart failure: physiology, pathophysiology, and clinical implications; Journal of the American College of Cardiology; 54(19); pp. 1747-1762; Nov. 3, 2009.

Iranitalab; U.S. Appl. No. 17/152,665 entitled "Methods and devices for endovascular ablation of a splanchnic nerve," filed Jan. 19, 2021.

Levin et al.; U.S. Appl. No. 17/171,447 entitled "Devices and methods for treatment of heart failure by splanchnic nerve ablation," filed Feb. 9, 2021.

Burchell et al.; Chemohypersensitivity and autonomic modulation of venous capacitance in the pathophysiology of acute decompensated heart failure; Current Heart failure Reports; 10(2); pp. 139-146; Jan. 2013.

Puntawangkoon et al.; Reduced peripheral arterial blood flow with preserved cardiac output during submaximal bicycle exercise in elderly heart failure; Journal of Cardiovascular Magnetic Resonance; 11(1); pp. 1-11; Dec. 2009.

Iranitalab et al.; U.S. Appl. No. 18/057,482 entitled "Methods and devices for endovascular ablation of a splanchnic nerve," filed Nov. 21, 2022.

\* cited by examiner

METHODS AND DEVICES FOR ENDOVASCULAR ABLATION OF A SPLANCHNIC NERVE

CROSS REFERENCE TO RELATED APPLICATIONS

This application is a continuation of U.S. application Ser. No. 16/222,823, filed Dec. 17, 2018, now U.S. Pat. No. 10,561,461, which claims the benefit of priority to the following U.S. provisional applications: App. No. 62/599,715, filed Dec. 17, 2017 and App. No. 62/660,258, filed Apr. 20, 2018, each of which is herein incorporated by reference in its entirety for all purposes.

INCORPORATION BY REFERENCE

All publications and patent applications mentioned in this specification are herein incorporated by reference to the same extent as if each individual publication or patent application was specifically and individually indicated to be incorporated by reference.

This document is related by subject matter to US Pub. No. 2018/0110561 and PCT Pub. No. WO2018/023132, which are incorporated herein by reference in their entireties for all purposes.

BACKGROUND

Heart failure (HF) is a medical condition that occurs when the heart is unable to pump sufficiently to sustain the organs of the body. Heart failure is a serious condition and affects millions of patients in the United States and around the world.

In the United States alone, about 5.1 million people suffer from heart failure and according to the Center for Disease Control, the condition costs the nation over $30 billion in care, treatments, medications, and lost production. The normal healthy heart is a muscular pump that is, on average, slightly larger than a fist. It pumps blood continuously through the circulatory system to supply the body with oxygenated blood. Under conditions of heart failure, the weakened heart cannot supply the body with enough blood and results in cardiomyopathy (heart muscle disease) characterized by fatigue and shortness of breath, making even everyday activities such as walking very difficult.

Oftentimes, in an attempt to compensate for this dysfunction, the heart and body undergo physiological changes that temporarily mask the inability of the heart to sustain the body. These changes include the enlargement of heart chamber, increased cardiac musculature, increased heart rate, raised blood pressure, poor blood flow, and imbalance of body fluids in the limbs and lungs.

One common measure of heart health is left ventricular ejection fraction (LVEF) or ejection fraction. By definition, the volume of blood within a ventricle immediately before a contraction is known as the end-diastolic volume (EDV). Likewise, the volume of blood left in a ventricle at the end of contraction is end-systolic volume (ESV). The difference between EDV and ESV is stroke volume (SV). SV describes the volume of blood ejected from the right and left ventricles with each heartbeat. Ejection fraction (EF) is the fraction of the EDV that is ejected with each beat; that is, it is SV divided by EDV. Cardiac output (CO) is defined as the volume of blood pumped per minute by each ventricle of the heart. CO is equal to SV times the heart rate (HR).

Cardiomyopathy, in which the heart muscle becomes weakened, stretched, or exhibits other structural problems, can be further categorized into systolic and diastolic dysfunction based on ventricular ejection fraction.

Systolic dysfunction is characterized by a decrease in myocardial contractility. A reduction in the LVEF results when myocardial contractility is decreased throughout the left ventricle. CO is maintained in two ways: left ventricular enlargement results in a higher SV and an increase in contractility as a result of the increased mechanical advantage from stretching the heart. However, these compensatory mechanisms are eventually exceeded by continued weakening of the heart and CO decreases, resulting in the physiologic manifestations of HF. The left side of the heart cannot pump with enough force to push a sufficient amount of blood into the systemic circulation. This leads to fluid backing up into the lungs and pulmonary congestion. In general terms, systolic dysfunction is defined as an LVEF less than 40% and heart failure in these patients can be broadly categorized as heart failure with reduced ejection fraction (HFrEF).

Diastolic dysfunction refers to cardiac dysfunction in which left ventricular filling is abnormal and is accompanied by elevated filling pressures. In diastole, while the heart muscle is relaxed the filling of the left ventricle is a passive process that depends on the compliance (defined by volume changes over pressure changes), or distensibility, of the myocardium or heart muscle. When the ventricles are unable to relax and fill, the myocardium may strengthen in an effort to compensate to poor SV. This subsequent muscle hypertrophy leads to even further inadequate filling. Diastolic dysfunction may lead to edema or fluid accumulation, especially in the feet, ankles, and legs. Furthermore, some patients may also have pulmonary congestion as result of fluid buildup in the lungs. For patients with HF but without systolic dysfunction, diastolic dysfunction is the presumed cause. Diastolic dysfunction is characteristic of not only hypertrophic cardiomyopathy (HCM), which is characterized by the thickening of heart muscle, but also restrictive cardiomyopathy (RCM), which is characterized by rigid heart muscle that cannot stretch to accommodate passive filling. In general terms, diastolic dysfunction is defined as a LVEF of greater than 40% and HF in these patients can be broadly categorized as heart failure with preserved ejection fraction (HFpEF).

While a number of drug therapies successfully target systolic dysfunction and HFrEF, for the large group of patients with diastolic dysfunction and HFpEF no promising therapies have yet been identified. The clinical course for patients with both HFrEF and HFpEF is significant for recurrent presentations of acute decompensated heart failure (ADHF) with symptoms of dyspnea, decreased exercise capacity, peripheral edema, etc. Recurrent admissions for ADHF utilize a large part of current health care resources and could continue to generate enormous costs.

While the pathophysiology of HF is becoming increasingly better understood, modern medicine has, thus far, failed to develop new therapies for chronic management of HF or recurrent ADHF episodes. Over the past few decades, strategies of ADHF management and prevention have and continue to focus on the classical paradigm that salt and fluid retention is the cause of intravascular fluid expansion and cardiac decompensation.

Thus there remains a need for improved therapies for heart failure patients that is safe and effective, and devices and systems that are adapted to perform those therapies.

SUMMARY OF THE DISCLOSURE

The disclosure is related to methods of, devices for, and approaches for ablating a thoracic splanchnic nerve or a thoracic splanchnic nerve root. The ablations can be performed to treat at least one of hypertension and heart failure, but the general methods may also be used for other treatments as well. For example, the methods herein can be used in the treatment of pain, or even to generally benefit the subject to reducing the amount of blood that is expelled from the splanchnic bed into the central thoracic veins.

The treatments herein may be accomplished by increasing splanchnic capacitance. The therapies generally include ablating a patient's preganglionic thoracic splanchnic nerve or thoracic splanchnic nerve branch to increase splanchnic capacitance, and thereby treat at least one of hypertension and heart failure.

Methods herein describe ablating thoracic splanchnic nerves, such as a greater splanchnic nerve or greater splanchnic nerve roots. While methods herein may provide specific examples of targeting greater splanchnic nerve or greater splanchnic nerve roots, it may be possible to alternatively, or in addition to, ablate other thoracic splanchnic nerves (e.g., lesser, least) to perform one or more treatments herein.

One aspect of the disclosure is a method of ablating tissue by positioning a medical device intravascularly in the vicinity of target tissue, and using the medical device to ablate tissue and create a lesion. One aspect of the disclosure a method of ablating tissue by positioning a medical device intravascularly into one or more target vessels, and using the medical device to ablate tissue and create a lesion. The methods herein can thus be described as methods that position a medical device near target tissue to be ablated and/or methods that position a medical device in one or more vessels, where the target tissue in relatively near to the target regions within the one or more vessels. Any of the method steps herein (including, for example without limitation, in the claims or the Description section) can be incorporated into any other method of use herein unless specifically indicated to the contrary herein.

One aspect of the disclosure is a method of ablating a greater splanchnic nerve or a greater splanchnic nerve root to increase splanchnic venous blood capacitance, the method including advancing a medical device into a first vessel, advancing the medical device into a second vessel, and delivering ablation energy from the medical device to create a lesion in tissue surrounding the first vessel.

In some embodiments the first vessel is an azygous vein and the second vessel is an intercostal vein.

In some embodiments an intercostal vein is one of the three lowest intercostal veins.

In some embodiments an intercostal vein is a T9, T10, or T11 intercostal vein.

The methods can include positioning a distal end of an ablation element in the second vessel and no more than 30 mm (e.g., 20 mm, 15 mm, 12 mm) from a junction between the first vessel and the second vessel when delivering the energy.

The methods can include a proximal portion of an ablation being disposed in the second vessel when delivering energy.

The methods can include delivering fluid from a fluid lumen of the medical device into a membrane, wherein the membrane at least partially defines a fluid chamber. Delivering the fluid can inflate the membrane and cause it to change configuration to an expanded configuration or state. Expanding the membrane may cause the membrane to have an outer diameter larger than a size of the vessel.

The methods can include positioning the ablation element into contact with a wall of the second vessel, optionally along the entire length of the ablation element, or at least along an active ablation length of the ablation element.

The methods can include expanding the membrane so that it has an outer diameter from 2 mm to 4 mm.

Creating the lesion can include creating a lesion that has a depth of at least 5 mm around the ablation element.

Creating the lesion can include ablating a portion of a thoracic splanchnic nerve or a thoracic splanchnic nerve root, e.g., a greater splanchnic nerve or GSN root.

The lesion may be a continuous lesion. The lesion may have a length from 5 mm to 20 mm, such as 10 mm to 20 mm, such as 12 mm to 18 mm.

The lesion may be a circumferential lesion all the way around the second vessel. The lesion may be less than circumferential all the way around the second vessel, such as 225 degrees or less, 180 degrees or less, 135 degrees or less, 90 degrees or less, 45 degrees or less.

The methods can include positioning an entire ablation element in the second vessel, while the method can also include positioning less than the entire length of the ablation element in the second vessel.

The methods can include performing an ablation process in more than one target vessel, such as an intercostal vein or an azygous vein. The methods of ablation herein can also be performed in the second vessel.

The methods can include performing an ablation confirmation test, such as any of the tests herein. If desired or needed, an ablation element may be repositioned into a second target vessel, which may be an azygous vein or a different intercostal vein.

The methods can create a continuous lesion that has a length from 1 mm to 20 mm, such as from 5 mm to 20 mm, such as from 10 mm to 20 mm.

The methods can include delivering hypertonic saline through the fluid lumen and into the volume at least partially defined by the membrane.

The methods can include communicating RF energy to an electrode disposed within the membrane, conducting RF energy to a conductive fluid in the membrane, through the membrane, and into tissue to thereby create a continuous lesion.

The methods herein can create an ionic communication between the membrane and tissue in apposition with an external surface of the membrane.

The methods can also include, prior to, during, and/or subsequent to delivering the ablation energy, delivering stimulation energy to first and second stimulation electrodes carried by the medical device. Delivering stimulation energy may help determine if the ablation element is in a target location within the intercostal vein, and/or if an ablation procedure was effective.

One aspect of the disclosure is a method of ablating a thoracic splanchnic nerve or a thoracic splanchnic nerve root to treat at least one of hypertension and heart failure, comprising: advancing an elongate medical device into an intercostal vein, the elongate medical device comprising an ablation member disposed at a distal region of the medical device; expanding the ablation member within the intercostal vein; activating the ablation member to create an electromagnetic field in tissue around the intercostal vein. The method can include heating tissue surrounding the intercostal vein to a temperature of up to 99 degrees C. and ablating a thoracic splanchnic nerve or a thoracic splanchnic nerve root.

One aspect of the disclosure is a method of transvascular ablation of target tissue, the method include delivering an ablation catheter through a patient's vasculature to a first vessel, the ablation catheter comprising at least one energy delivery element; advancing the at least one energy delivery element into a second vessel, the second vessel directly connecting to the first vessel; and delivering ablation energy from the at least one energy delivery element to the target tissue. The ablation catheter can include at least one RF electrode that has a diameter that is within 1 mm of the diameter of the second vessel (e.g., within 1 mm less than or greater than the diameter of the second vessel).

The energy delivery element can include an RF electrode, microwave antenna, ultrasound transducer, cryogenic applicator, and/or thermal element. The step of advancing the at least one energy delivery element can include advancing a distal end of the energy delivery element no more than 30 mm, such as no more than 20 mm, into the second vessel from the first vessel. In an embodiment the at least one energy delivery element has the same diameter during the step of advancing and the step of delivering ablation energy. In some embodiments the at least one energy delivery element has a greater diameter during the step of delivering ablation energy than the advancing step.

Any of the other method steps herein that are described in the context of other methods can be performed with this exemplary method.

Another aspect of the disclosure is a method of transvascular ablation of a greater splanchnic nerve comprising the following steps: delivering an ablation catheter comprising a distal region, an ablation element on the distal region, and two nerve stimulation electrodes positioned distal and proximal to the ablation element to an intercostal vein; positioning the ablation element in a target region within the intercostal vein; measuring a first physiological condition without delivering energy from the ablation catheter to establish a baseline response; delivering a nerve stimulation signal in bipolar mode to the two nerve stimulation electrodes; measuring a second physiological condition during the nerve stimulation signal delivery; if the second physiological condition shows an increased sympathetic response compared to the first physiological condition, then delivering ablation energy from the ablation element; following or during ablation energy delivery, delivering a second nerve stimulation signal and measuring a third physiological condition; if the third physiological condition shows a decreased sympathetic response compared to the first physiological condition, removing the catheter from the patient; adjusting the position of the ablation element within the intercostal vein or moving it to a different intercostal vein and repeating the steps between delivering the nerve stimulation signal to delivering ablation energy if the second physiological condition does not show an increased sympathetic response compared to the first physiological condition; moving the ablation element to an adjacent intercostal vein and repeating the steps between delivering the nerve stimulation signal to delivering ablation energy if the third physiological condition does not show a decreased sympathetic response compared to the first physiological condition.

A physiological condition may be, for example, venous compliance and the measuring may comprise a leg raise test, a hand-grip test, and/or a test that activates SNS.

Any nerve stimulation signals herein may comprise, for example, 50 Hz and 1 V.

One aspect of the disclosure is a method that includes delivering an ablation catheter comprising an energy delivery element (or member) through a venous system of the patient, positioning the energy delivery element at least partially (optionally completely) inside a vein selected from T9, T10 and T11 intercostal veins, delivering ablation energy from the energy delivery element to create a continuous lesion having a depth of at least 5 mm and a length from 10 to 20 mm. The continuous lesion and its parameters can be formed by selecting or choosing certain energy delivery parameters that will create the lesion. In some embodiments, the lesion can extend from an ostium of an azygos vein to up to 20 mm along the intercostal vein.

Any of the other method steps herein that are described in the context of other methods can be performed with this exemplary method.

In some alternative methods herein, a plurality of ablations (i.e., from ablation energy on to energy ablation off) can be performed within a single target vessel (e.g., an intercostal vein) to create a total lesion made from two or more lesions made from the plurality of ablations. The total lesion made from the plurality of lesions can have any of characteristics of the other lesions herein. For example, the total lesion can be continuous (made by the connection of a plurality of lesions created during different ablations), can be up to 20 mm long, can be circumferential (or not), etc. After a first ablation, the ablation device can be moved within the same vessel and create a second lesion, which may or may not overlap with a first lesion. This can be repeated as many times as desired. Any of the stimulation or testing steps herein can be performed before, during, or after any ablation step, even if a plurality of ablations are performed in a single vessel.

One aspect of the disclosure is an ablation device (e.g., an ablation catheter) adapted for endovascular ablation of a patient's greater splanchnic nerve or a greater splanchnic nerve root. The device may include a flexible shaft having a distal section and a proximal section, at least one ablation element carried by the distal section (directly or indirectly), wherein the at least one ablation element has an active ablation length from 1 mm to 20 mm (optionally from 5 mm to 20 mm) and an outer diameter from 2 mm to 4 mm. The active ablation length may be from 10 mm to 20 mm, e.g., 12 mm to 18 mm.

One aspect of the disclosure is an ablation device for endovascular ablation of a patient's greater splanchnic nerve or a greater splanchnic nerve root, including a flexible shaft having a distal section and a proximal section; a fluid lumen extending through at least a portion of the flexible shaft; and at least one ablation element disposed at the distal section, the at least one ablation element comprising a membrane with an active ablation length from 1 mm to 20 mm (e.g., from 5 mm to 20 mm) and an outer diameter from 2 mm to 4 mm, the membrane defining an interior volume in fluid communication with the fluid lumen.

One aspect of the disclosure is an ablation device adapted for endovascular ablation of a patient's greater splanchnic nerve or a greater splanchnic nerve root, including a flexible shaft having a distal section and a proximal section; a fluid lumen extending through at least a portion of the flexible shaft; and at least one ablation member disposed at the distal section, the at least one ablation member comprising a balloon defining an interior volume in fluid communication with the fluid lumen, wherein the flexible shaft and at least one ablation member are sized and configured to position the at least one ablation member in an intercostal vein, and wherein the at least one ablation member is configured and constructed to create a circumferential lesion around the a blood vessel.

One aspect of the disclosure is an ablation device for endovascular ablation of a patient's greater splanchnic nerve or a greater splanchnic nerve root comprising: a flexible shaft having a distal section and a proximal section; at least one ablation membrane disposed at the distal section; wherein the at least one ablation membrane has an inflated configuration that is cylindrical with an outer diameter of 2 mm to 4 mm, and has a plurality of pores sized to prevent the passage of water but allow the passage of sodium ions.

One aspect of the disclosure is an ablation device for endovascular ablation of a patient's greater splanchnic nerve or a greater splanchnic nerve root, the device comprising a flexible shaft having a fluid supply lumen, a distal section, and a proximal section, at least one ablation element mounted at the distal section, wherein the at least one ablation element comprises a membrane presenting an active ablation length and an outer diameter, the ablation element being configured to receive conductive fluid through said fluid supply lumen, wherein the at least one ablation element comprises an active ablation length from 5 to 20 mm, and an outer diameter from 2 to 4 mm.

With any of the ablation devices herein, the ablation element can be adapted and configured to create a circumferential lesion around a blood vessel in which it is placed.

With any of the ablation devices herein, the ablation element can be adapted and configured to create a lesion less than circumferential around a blood vessel in which it is placed.

With any of the ablation devices herein, an active ablation length of the at least one ablation element can be from 10 mm to 20 mm, such as from 12 mm to 18 mm.

With any of the ablation devices herein, a distal section of a flexible shaft can be adapted and configured to bend at a bend angle of at least 90 degrees and with a bend radius of between 4 mm and 15 mm.

With any of the ablation devices herein, the at least one ablation element can be adapted and configured to have a delivery configuration with a length from 5 mm to 20 mm and an outer diameter from 1.5 mm to 2.5 mm.

With any of the ablation devices herein, the device can further include a proximal stimulation electrode positioned proximal to an ablation element, and a distal stimulation electrode positioned distal to an ablation element, optionally wherein each of the proximal stimulation electrode and the distal stimulation electrode are no more than 5 mm from the ablation element.

With any of the ablation devices herein, the device can further include a proximal stimulation electrode positioned proximal to an ablation element, and a distal stimulation electrode positioned distal to an ablation element, wherein the proximal stimulation electrode and the distal stimulation electrode can be separated by a distance of no more than 25 mm.

With any of the ablation devices herein, a flexible shaft can comprise a fluid lumen in fluid communication with at least one ablation element that comprises a membrane that at least partially defining an interior volume, the interior volume in fluid communication with the fluid lumen.

With any of the ablation devices herein, a membrane can have an expanded configuration, and an interior volume of an ablation element can be from 24 mm3 to 141 $mm^3$.

With any of the ablation devices herein, a membrane may be, for example, a microporous membrane, an electrically conductive membrane, a capacitive coupling membrane, or a weeping membrane.

With any of the ablation devices herein, an active ablation length may be between 12 and 18 mm.

With any of the ablation devices herein, a distal section of said flexible shaft may be configured to bend according to a bend angle of at least 90 degrees and a bend radius of between 4 mm and 15 mm.

With any of the ablation devices herein, an ablation element may be configurable in at least one delivery state and in at least one deployed state, wherein in the delivery state the ablation element is radially more contracted than in the deployed state. The ablation element in the delivery state may have at least one of the following: a length from 5 and 20 mm; an outer diameter from 1.5 to 2.5 mm. The ablation element in the deployed state may define an internal cavity configured for receiving conductive fluid, wherein the internal cavity may have a volume comprised between 15 and 252 $mm^3$.

With any of the ablation devices herein, an ablation element may have a single non-deployable configuration. The non-deployable ablation element may define an internal cavity configured for receiving fluid (e.g., conductive fluid), wherein the internal cavity has a volume from 15 and 252 $mm^3$.

With any of the ablation devices herein, the device may further include at least one temperature sensor, optionally positioned inside an ablation element. The at least one ablation element and the at least one temperature sensor may be connectable to an ablation energy source.

With any of the ablation devices herein, a membrane is configured to deliver RF energy, for example via conduction, capacitive coupling or selective passage of ions.

With any of the ablation devices herein, a membrane is a microporous membrane having pores in a range of 100 to 150 picometers.

With any of the ablation devices herein, a membrane may be configured to allow diffusion of sodium ions and not allow diffusion of water molecules.

With any of the ablation devices herein, one or more nerve stimulation electrodes may be 1.5 mm +/−0.5 mm long.

With any of the ablation devices herein, the device may further comprise a temperature sensor exterior to the ablation element, which can include being carried by a surface of an ablation element.

With any of the ablation devices herein, an ablation element can be configured to emit ablative energy from a segment of the circumference of the distal region. For example, the segment may be a percentage of the circumference selected from a list of 50%, 40%, 30%, or 25% of the circumference. The segment can also be described as an angle, such as less than 225 degrees, 180 degrees or less, 135 degrees or less, 90 degrees or less, or 45 degrees or less. The remainder of the circumference not adapted to emit ablative energy may optionally comprise an electrically resistive material (e.g., disposed on or within a membrane layer). Optionally, the segment can be defined by a fenestration in a sheath. The distal region of the device may further comprise a radiopaque marker configured to indicate radial orientation. For example, the radiopaque marker may be radially aligned with the segment adapted to emit ablative energy.

With any of the ablation devices herein, one or more temperature sensors may be positioned in the cavity to monitor temperature of a conductive fluid, an RF electrode, or a membrane.

With any of the ablation devices herein, a distal tip may be tapered to facilitate delivery from a first vessel to a second vessel having a smaller lumen diameter.

With any of the ablation devices herein, the device can further comprise a distal tubular extension having greater flexibility than an elongate tubular shaft, and wherein a guidewire lumen optionally extends through the distal tubular extension.

With any of the ablation devices herein, the active ablation length of the ablation element is considered the length of the ablation element that is in contact with, or configured to be in contact with, tissue during an ablation step.

An exemplary ablation device comprises an elongate tubular shaft having a proximal end, a distal end, and a distal section positioned toward the distal end, a guidewire lumen extending through the elongate tubular shaft, a fluid delivery lumen extending from the proximal end to the distal region, and an ablation element positioned on the distal region, the ablation element comprising a microporous membrane at least in part defining a cavity, an electrode positioned in the cavity, and a fluid delivery port positioned in the cavity and in fluid communication with the fluid delivery lumen. The distal section may be configured to bend according to a bend angle of at least 90 degrees with a bend radius in a range of 4 to 15 mm. The microporous membrane may define a complete circumference of the ablation element. Alternatively, the microporous membrane may define a segment of a circumference of the ablation element. The microporous membrane may define an outer surface of the ablation element, the ablation element having an active ablation length in a range of 5 mm to 20 mm and an outer diameter in a range of 2 mm to 4 mm. The ablation element may be deployable between a delivery state and a deployed state, the delivery state having a maximum diameter of 2.5 mm and a length in a range of 5 mm to 20 mm, the deployed state having a maximum diameter in a range of 2.5 to 4 mm and a length in a range of 5 mm to 20 mm. The ablation element in the deployed state may define an internal cavity configured for receiving said conductive fluid, wherein the internal cavity has a volume comprised between 15 and 252 mm$^3$. The ablation element may be tapered at its distal and proximal ends. The microporous membrane can have pores with a diameter in a range of 100 to 150 picometers (i.e., 0.1 to 0.15 nanometers). Optionally, the electrode may be made from an electrically conductive material having a form of a coiled wire, wire strands, or a laser cut tube. The device may optionally further comprise a fluid return lumen in fluid communication with a fluid return port positioned in the cavity allowing closed circuit flow of conductive fluid. The device may further comprise at least one nerve stimulation electrode, which may be positioned on the outer surface of the microporous membrane or on the shaft of the catheter.

With any of the devices herein, a microporous membrane may define a segment of a circumference of the ablation element.

BRIEF DESCRIPTION OF THE DRAWINGS

The drawings included herewith are for illustrating various examples of articles, methods, and apparatuses of the present specification and are not intended to limit the scope of what is taught in any way. In the drawings.

DETAILED DESCRIPTION

Figure 1:
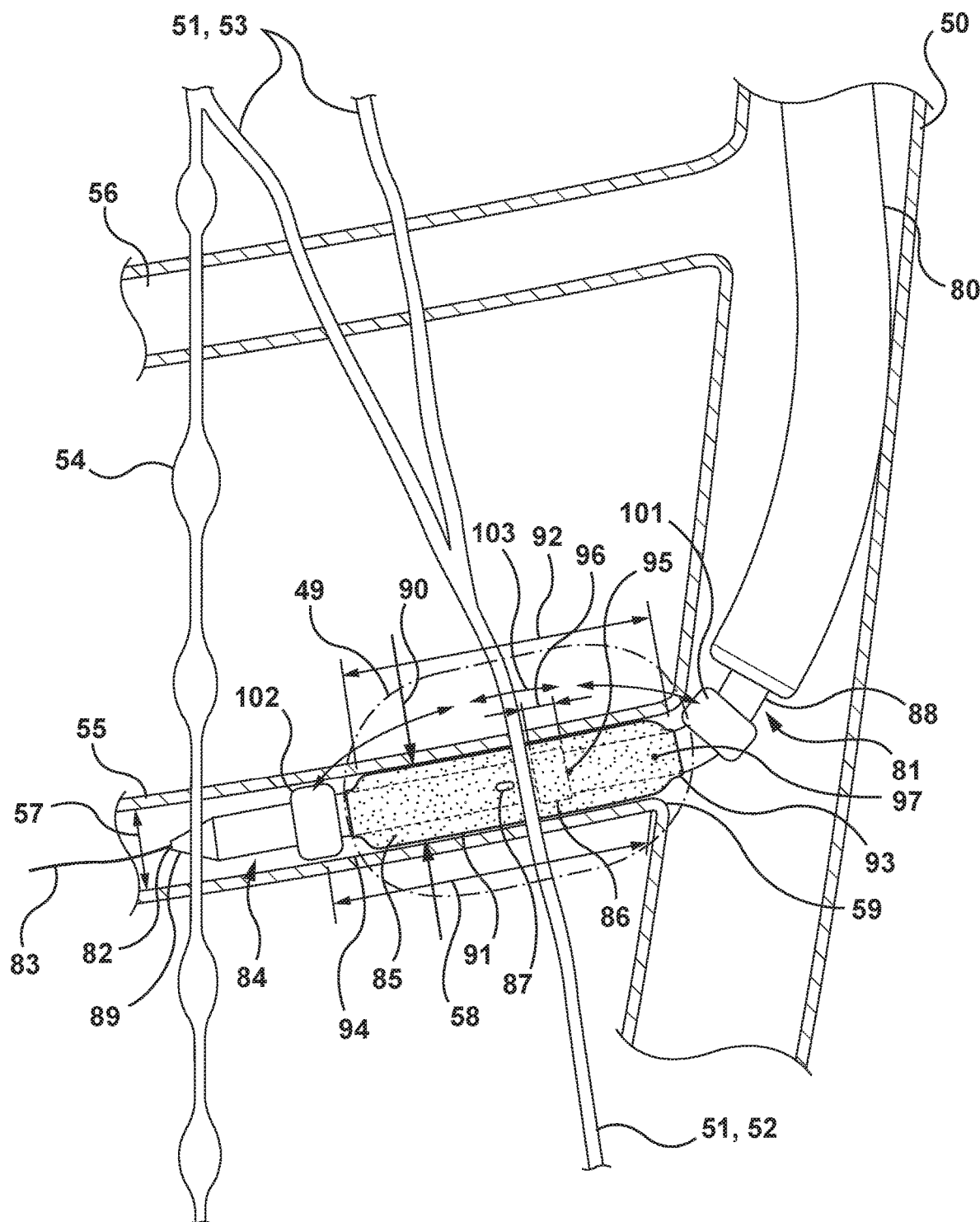
FIG. 1 is a schematic illustration of an ablation catheter positioned in an intercostal vein for ablation of a thoracic splanchnic nerve.

This disclosure is related by subject matter to the disclosure in U.S. Pub. No. 2018/0110561 and PCT Pub. No. WO2018/023132, which are incorporated herein by reference in its entirety for all purposes.

The disclosure herein is generally related to methods of treating at least one of heart failure and hypertension by increasing splanchnic capacitance. Some approaches include systems, devices, and methods for transvascular (e.g., transvenous) ablation of target tissue to increase splanchnic capacitance. The devices and methods may, in some examples, be used for ablating a splanchnic nerve to increase splanchnic capacitance. For example, the devices disclosed herein may be advanced endovascularly to a target vessel in the region of a thoracic splanchnic nerve ("TSN"), such as a preganglionic greater splanchnic nerve ("GSN"), lesser splanchnic nerve, or least splanchnic nerve or one of their roots (a TSN nerve root). The target vessel may be, for example, an intercostal vein or an azygos vein (or both) or a vein of the azygos vein system, preferably, one or more of the lowest (i.e., most caudal) three intercostal veins (which may be T9, T10, and T11). A target region in a target vein for example may include a lumen in an intercostal vein, and can be a region that does not extend more than 30 mm into the vein from the adjoining azygos or hemiazygos vein, and optionally does not extend more than 20 mm into the vein from the adjoining azygos or hemiazygos vein. The target region thus has a distal end that is not further than a particular distance (or range of distances) from the ostium. Methods of use herein that position an ablation element (or ablation member generally) in a target region of a vessel are therefore not limited to requiring that the entire length of the ablation element is positioned in the target vessel, but rather they include methods in which a proximal portion, perhaps a relatively small portion thereof (e.g., less than 25% of the length) is still positioned in an adjacent vessel (e.g., an azygous vein). Methods herein that describe placing an ablation element or member in a target vessel within a certain distance from an ostium are therefore generally describing positioning a distal end of the ablation element within the target region of the target vessel, regardless of whether the entirety of the ablation element is within the same vessel (e.g., intercostal vein) or whether a portion is disposed in an adjacent vessel (e.g., azygous vein). In any of the methods herein, less than 50% of the length of the ablation element may be positioned in the adjacent vessel, such as less than 45%, or less than 40%, or less than 35%, or less than 30%, or less than 25%, or less than 20%, or less than 15%, or less than 10%.

The therapy devices may comprise an ablation element comprising a membrane defining at least a portion of the ablation element's outer surface. Optionally, the ablation element is delivered in a contracted (or unexpanded) delivery state and may be deployed once placed in a target region of a target vessel to an expanded deployed state. In some embodiments the ablation element has a maximum diameter close to or greater than the target vessel lumen diameter and may be squeezed into the vessel. Ablation of the TSN may be carried out for example by radiofrequency (RF) ablation transmitted through or from the membrane to tissue. Ablation of the TSN may affect circulating blood volume, pressure, blood flow and overall heart and circulatory system functions, in order to treat at least one of heart failure and hypertension, which is described in more detail in PCT Pub. No. WO2018/023132. Ablation of the TSN may also have therapeutic benefits such as treating intractable abdominal pain or motility.

Other applications of the devices disclosed herein may be envisioned, in particular for transvascular tissue ablation from within a small body lumen (e.g., artery, vein, blood vessel, airway, urethra, lumen having a diameter less than 4 mm).

A TSN may be up to 5 mm from a target intercostal vein in most humans. Intercostal veins at the lower levels (e.g., T9, T10, T11 levels) may have inner lumens in the target regions having a diameter range of 2 to 3.5 mm. A TSN, in particular a fully formed GSN, may traverse a target intercostal vein in the target region between an adjoining azygos or hemiazygos vein and a distance of no more than 15 mm from the adjoining azygos or hemiazygos. Beyond a distance of 20 mm from the adjoining azygos or hemiazygos a sympathetic trunk may traverse the intercostal vein.

Ablation of a TSN by thermal coagulation may involve heating tissue with an ablation element positioned in the target intercostal vein, which presents various technical challenges. Thermal ablation from a small vein can cause the vessel to shrink during energy delivery, which can drastically alter the thermal and electrical environment of an ablation element, particularly if the vessel shrinks around the ablation element, for example caused by a significant change in tissue contact or blood flow, making energy delivery erratic and ablation less predictable or controlled.

With devices and methods disclosed herein, the TSN may be ablated in a relatively safe manner, with minimal or reduced adverse effects (such as damage to the lungs or other nerves). Some method of use embodiments herein may temporarily occlude blood flow and reduce an effect of vein collapse, thus advantageously avoiding challenges of a changing thermal and electrical environment during the heating process. Some method of use embodiments herein may ablate a nerve up to 5 mm from the target vessel. Some of the devices herein are dimensioned and configured for delivery and positioning in vasculature specified for ablating a target nerve (e.g., TSN, GSN).

Some of the devices herein may have one or more features that provides for a safe delivery to the target vessel.

Some of the devices and methods of use herein may safely deliver energy with temperature monitored energy delivery.

Some of the methods of use herein may generate a lesion capable of targeting a nerve up to 5 mm away from the target vessel and within a target region having a continuous lesion length of up to 20 mm (e.g., 15 mm, 12 mm) with a single positioning and delivery of energy.

Some of the devices and methods herein are adapted to avoid risks of boiling, hot spots, or erratic energy delivery that could decrease ablation efficacy. Furthermore, some embodiments may include nerve stimulation to identify a target nerve or non-target nerve to confirm positioning prior to ablation, or to confirm technical success during or following ablation.

FIG. 1 illustrates an exemplary method that includes positioning an exemplary elongate medical device 81 (e.g., a catheter) in an exemplary target location 58 in an exemplary intercostal vein 55. Any of the methods of delivering a medical device toward an intercostal vein described in any of FIGS. 25A-B, 38A-G, 39A-B, 40, or 41A-B from WO2018/023132 (incorporated by reference herein) can be used with any of the methods of use herein. Medical device 81 is advanced though azygous vein 50 and into intercostal vein 55, optionally using an over the wire procedure over guidewire 83, which was previously advanced into position into intercostal vein 55. An endovascular access route may include introduction into a femoral vein, radial vein, brachial vein, subclavian vein, or jugular vein); advancement to the inferior vena cava if introduced to a femoral vein, or superior vena cava if introduced to the superior veins; then advancement to the azygos vein 50 just below the bifurcation of the left and right innominate vein; if treating the right side the access route may pass down the azygos vein 50 to an target intercostal vein on the right side (e.g., an intercostal vein at level T11 55, T10 56, T9 (not shown), or any of the most caudal intercostal veins); if treating the left side, the access route may pass from the azygos vein to the hemiazygos vein 43, which is approximately at the level of the T8 vertebra, and to a target intercostal vein on the left side (e.g., an intercostal vein at level T11 55, T10 56, T9 (not shown), or any of the most caudal intercostal veins). The elongate medical device includes an ablation member that is positioned in a particular region within the intercostal vein, and within one of a particular number of intercostal veins (e.g., the lower three intercostal vein), so that when the ablation member is activated and ablation energy is delivered, the ablation energy will be delivered to form a lesion that includes a location with the target nerve (e.g., a thoracic splanchnic nerve, which in this example is a greater splanchnic nerve or greater splanchnic nerve roots) is located, or is very likely to be located based on the cadaver studies that have been performed to inform this disclosure.

Studies performed to inform this disclosure indicated that the lowest three intercostal veins are likely best positioned for the placement of the medical ablation devices because the TSN, GSN or GSN roots (target nerves) are very likely to cross one or more of the lowest three intercostal veins between the ostium to the azygos vein and within a particular distance from the ostium. One aspect of this disclosure is thus a preferred method that includes positioning the medical devices (at least an ablation member portion thereof) in one of a particular number of intercostal veins, and additionally within a particular distance from the ostium of the azygous vein. This location and placement will provide the highest likelihood that, when activated, the medical device will effectively ablate the target nerves, described in more detail below.

It may be preferred, but not required, that the methods of ablation create a continuous ablation zone (i.e., not having separate, discrete regions of ablated tissue that are not connected to each other). This ensures that the region of tissue where the target GSN nerve or GSN nerve root is likely to be located is most likely to be effectively ablated by the ablation energy. The continuous ablation zone may be circumferential, or less than circumferential.

It may also be preferred, but not required, that the methods of ablation create an ablation zone that has a depth of at least 5 mm and a length in a range of 5 to 20 mm, and preferably in the range of 10 to 20 mm. Ablation regions or zones with these parameters increase the likelihood that the ablation region will include the target GSN or GSN root. While this disclosure generally describes lesions with a length in the range of 5-20 mm, it may be possible to effectively ablate a target nerve with a lesion that has a length of less than 5 mm, such as between 1 mm and 5 mm. For example, some target nerves may be quite close to an ostium between, for example, an azygous vein and an intercostal vein, and it may be acceptable to create an ablation region or zone with a length of less than 5 mm and still effectively ablate the target nerve. Unlike treatments that are targeting nerves that innervate a vessel (e.g., some renal denervation approaches), these exemplary methods of treatment are targeting one or more target nerves that are in relatively close proximity to the intercostal vein and traverse or cross, rather than follow, the vein. Traverse in this context does not mean the nerve passes through the vein structure in any way, but rather refers to the general relative orientation of the nerves and veins.

It is understood that while some methods herein create a lesion that has a length within a particular range, the methods may inherently create these ablation lengths even if the length of the ablation zone is not a direct input to a procedure. For example, if a console or energy generator is used to deliver energy, one or more delivery parameters may be selected as part of the procedure (e.g., time, power, etc.), and ablation length is not necessarily an input to the procedure. This means that the ablation zone length may occur as a result of a procedure, even if the length is not particularly selected by a user or is not input to an energy generating device such as a generator. If a result of a procedure is that a lesion is created with a length in the ranges herein (or even likely to be created with a length in the ranges herein, then the method is understood to fall within the scope of a claim that includes an ablation zone length.

FIG. 1 illustrates exemplary device 81 that is adapted and configured for transvascular ablation of a target nerve (e.g., GSN 52, GSN roots 53, TSN 51) from a small vein (such as the lower three intercostal veins; e.g., T11 intercostal vein 55, T10 intercostal vein 56, T9 intercostal vein (not shown). Device 81 includes an elongate shaft 88, a catheter proximal portion (not shown) that is sized and configured to remain outside of the patient in use and may be manipulated by a physician, and a catheter distal portion 84 comprising at least one ablation element 91. An "ablation element" in this disclosure may be referred to as being part of a general "ablation member" even if the term ablation member is not specifically used.

FIG. 1 shows medical device 81 positioned in both an azygos vein 50 and an intercostal vein 55, wherein an ablation member (which in this embodiment includes ablation element 91) that is disposed at a distal section of the device 81 is positioned in the intercostal vein 55 and with a very small portion thereof at the ostium. Even if a proximal portion of the ablation member is disposed at or in the ostium, the ablation member is still considered to be in the intercostal vein. In this embodiment ablation element 91 is disposed at a distal section of shaft 88. As set forth above, in any of the methods herein, the entire length of the ablation element need not be positioned in the same vein as the distal end of the ablation member. For example, as set forth above, any ablation process can be carried out with a proximal portion of any of the ablation members herein positioned in an azygous vein while a distal end of the ablation member is in an intercostal vein. In any methods of use herein, when an ablation element or member is described as being within a certain distance of a junction between two vessels (e.g., a junction of an intercostal vein and an azygous vein), it is understood to mean that a distal end of the ablation element or member is within that distance, even if the proximal end is not within the same vessel.

In the example shown, device 81 (which in this example is a catheter) includes a guidewire lumen (not shown) extending therethrough, and the catheter distal portion 84 includes a guidewire exit port 82 positioned at or near the distal end of the distal section 84, so that the catheter 81 can be advanced into the venous system along a guidewire 83 (generally described elsewhere herein). In some examples, the elongate shaft 88 can include a braided shaft to facilitate torquability (i.e., transmission of torque from the catheter proximal portion to the catheter distal portion 84), particularly over a tortuous delivery path. In alternative examples, the guidewire lumen and exit port 82 may be omitted from the device, and exemplary methods may include advancing the catheter into a patient's cardiovascular system (e.g., into a vein or artery) without the aid of a guidewire. For example, a catheter may have a deflectable distal tip that is specifically adapted to bend to navigate the ostium and make a turn into the vein (e.g., a 90 degree deflectable bend with a bend radius in a range of 6 to 15 mm) to facilitate advancement from a first vein into a second vein (e.g., from an azygous vein into an intercostal vein, an example of which is shown in FIG. 1). Some devices that are used to ablate tissue in other regions of the body may have a rigid tip or rigid distal region. In general, that type of design is likely to be unfavorable in certain methods herein as it may be quite difficult to navigate a bend, and/or those devices may distort the anatomy significantly when attempting to access a target vessel.

Figure 4:
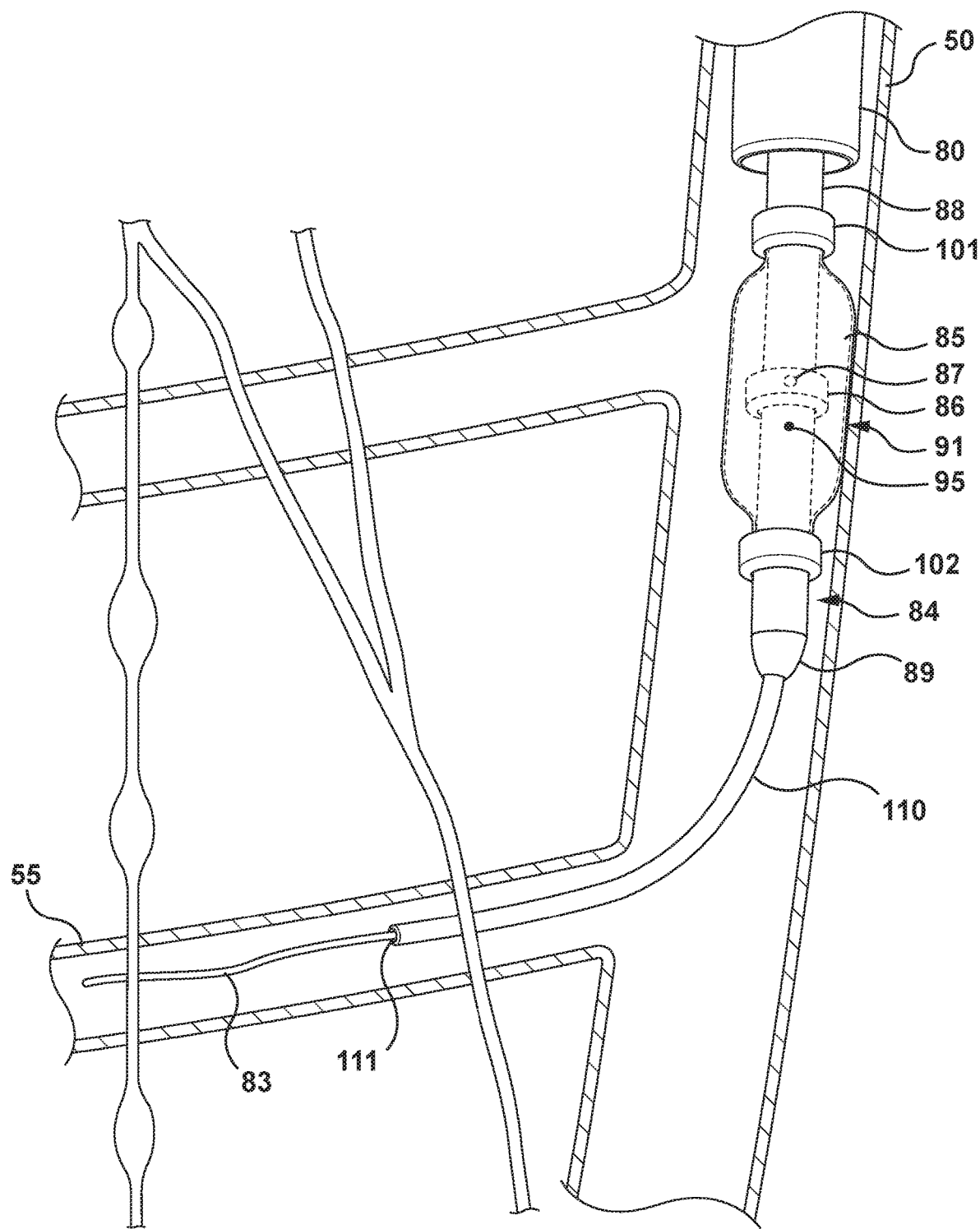
FIG. 4 is a schematic illustration of an ablation catheter being advanced over a guidewire from an azygos vein to an intercostal vein.

As shown in FIG. 4, to facilitate delivery of a distal section 84 of an ablation catheter over a tight bend, for example from an azygos vein 50 to an intercostal vein 55 or other tight bend from a small vessel (e.g., having a diameter in a range of 4 to 6 mm) to a second small vessel (e.g., having a diameter in a range of 2 to 4 mm) across an angle in a range of 45 degrees to 100 degrees, the catheter may optionally comprise a distal extra-flexible section 110 that extends distal to and from the tapered end 89 of the shaft 88 for example a length in a range of 10 mm to 40 mm. Parts of the device that can be the same as the device in FIG. 1 have the same reference numbers. The distal extra-flexible section 110 may comprise a lumen 111 for passing over a guidewire 83 and may be made of a flexible tube that passes through the shaft 88 to the proximal end of the catheter where it is available for accessing the lumen 111 for guide wire delivery. Optionally, the flexible tubular member 110 may be positioned in a fluid delivery lumen of the shaft 88 and have an outer diameter (e.g., about 0.022"+/−0.002") that is smaller than the inner diameter of the fluid delivery lumen leaving sufficient space in the fluid delivery lumen for delivery of fluid. A potting of adhesive may seal the fluid delivery lumen around the distal extra-flexible section 110 in a region between a fluid delivery port 87 and distal end of shaft 88. The distal extra-flexible section 110 may be a polymer that bends without kinking such as polypropylene, polyethylene, polyurethane, PEBAX® and the like. The inner diameter of lumen 111 may be sufficient to slidably pass over a guidewire. For example, an extra-flexible section 110 compatible with a guidewire having a diameter of about 0.014" may have an outer diameter of about 0.022", or a section 110 compatible with a guidewire having a diameter of about 0.038" may have an outer diameter of about 0.046".

Ablation element 91 shown in FIG. 1 comprises a membrane 85 attached to the shaft 88 of the catheter 81 at a proximal end 93 and distal end 94 of the ablation element for example with adhesive, crimps or heat shrink. The proximal end 93 and distal end 94 of the ablation element may be tapered from a smaller diameter of the shaft 88 to a larger diameter 90 of the ablation element. The membrane 85 defines an outer boundary of a cavity within the membrane through which the shaft 88 may pass. Within the cavity a fluid delivery port 87 is positioned and is in fluid communication with a fluid delivery lumen (not shown) extending from the fluid delivery port 87 to the proximal end of the catheter for delivery of an electrically conductive fluid such as hypertonic saline to the cavity. Optionally, a fluid return port 97 may be positioned in the cavity and in fluid communication with a fluid return lumen (not shown) extending to the proximal end of the catheter and the conductive fluid may be circulated prior to or during delivery of ablation energy. Having a fluid return lumen in addition to a fluid delivery lumen may allow conductive fluid to flow in and out of the cavity during delivery of ablation energy. Fluid flow may provide beneficial functions such as allowing greater ablative power to be delivered by avoiding fluid overheating, avoiding thermal injury of the vessel endothelium, or preventing the membrane from sticking to the tissue or to itself. Alternatively, any of the medical devices herein may not have a fluid supply lumen extending through the catheter, and conductive fluid may be injected into the cavity prior to use. For example, conductive fluid may be injected with a syringe through a self-sealing (e.g., silicone) injection port that may be near the distal region and in fluid communication with the cavity of the ablation element 91.

An RF electrode 86 is positioned within the cavity and, for example, disposed on the shaft 88. In use, RF energy is delivered to the RF electrode 86, conducted to the conductive fluid within the cavity, through the membrane, and through tissue to a dispersive return electrode for example placed on the patient's skin. In alternative embodiments, a dispersive return electrode may be positioned in the patient's body, for example on a delivery sheath (e.g., on delivery sheath 80) used to deliver the ablation catheter. The RF electrode 86 is electrically connected via a conductor passing through the catheter shaft 88 to the proximal end of the catheter where it is connectable to an energy source for example with an electrical connector. The function of the RF electrode 86 is to conduct RF energy from an energy source to the conductive fluid (e.g., hypertonic saline) and thus is made from an electrically conductive material such as stainless steel. Optionally, the RF electrode is radiopaque and for example, may contain platinum iridium. Preferably, the RF electrode does not hinder the ablation element from bending over a bend radius in a range of 4 m to 15 mm. The RF electrode 86 may have a relatively short length 96 as shown in FIG. 1 (e.g., in a range of 2 to 5 mm) particularly if the RF electrode has a rigid construction such as a band electrode as shown. Optionally, the fluid delivery port 87 or fluid return port 97 may be positioned on an RF electrode 86 so conductive fluid can be passed directly through the electrode as shown in FIG. 4.

Figure 5:
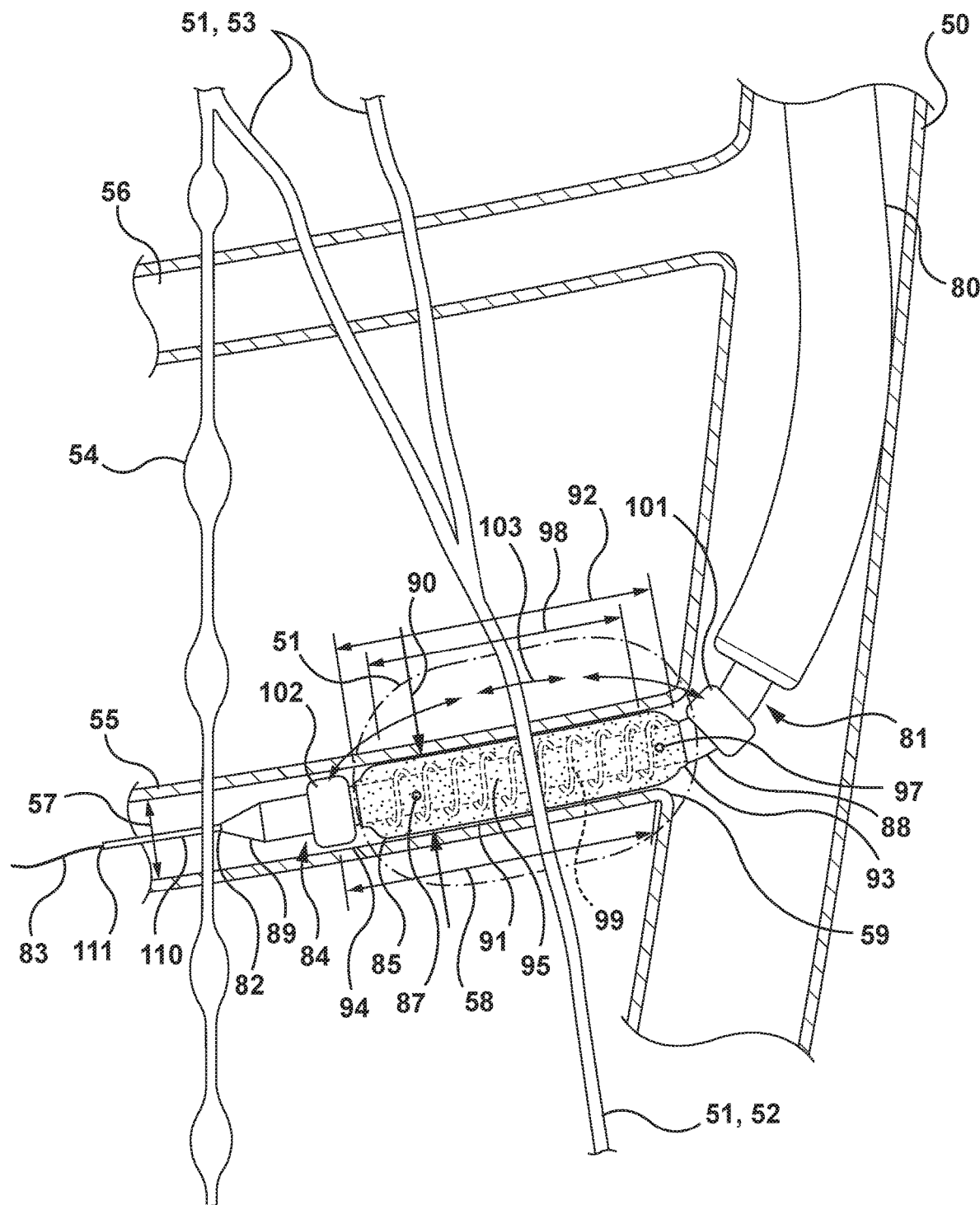
FIG. 5 is a schematic illustration of an ablation catheter having a coiled RF electrode.
Figure 6A:
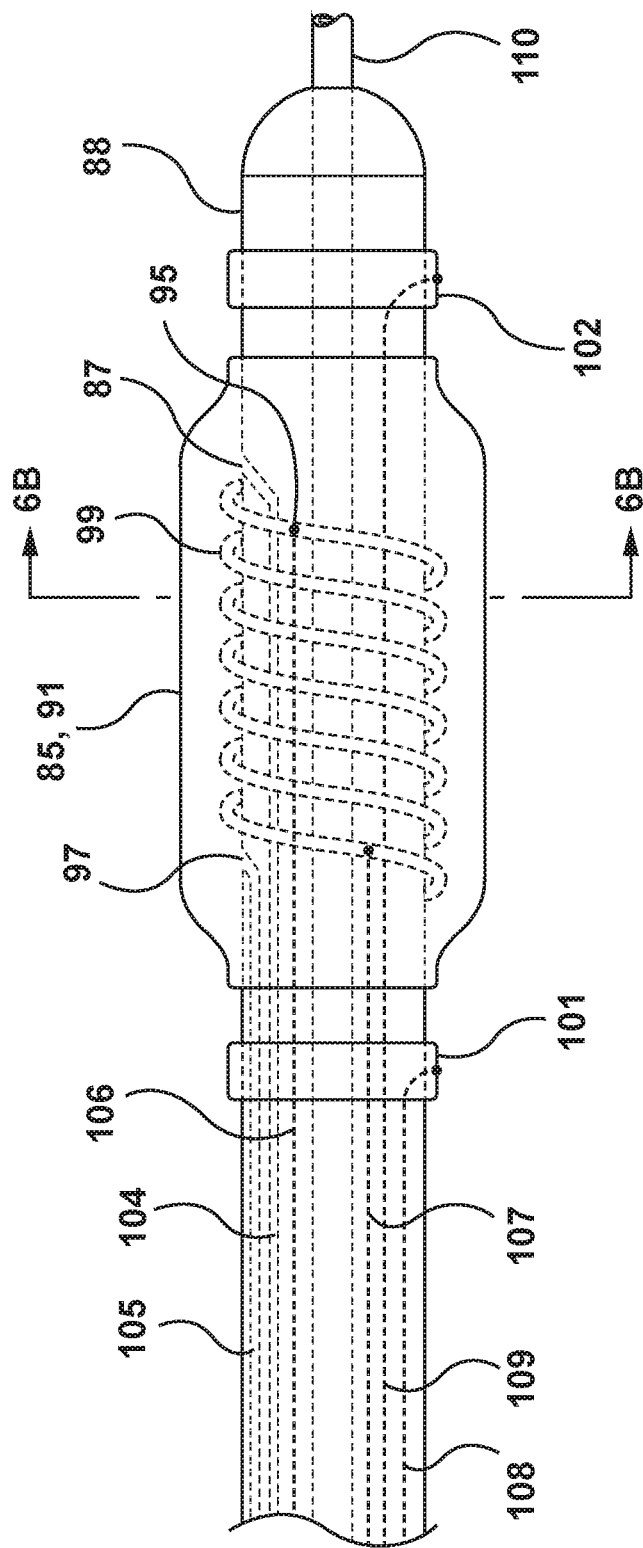
FIG. 6A is a schematic illustration of an ablation catheter of FIG. 5 showing internal components.
Figure 6B:
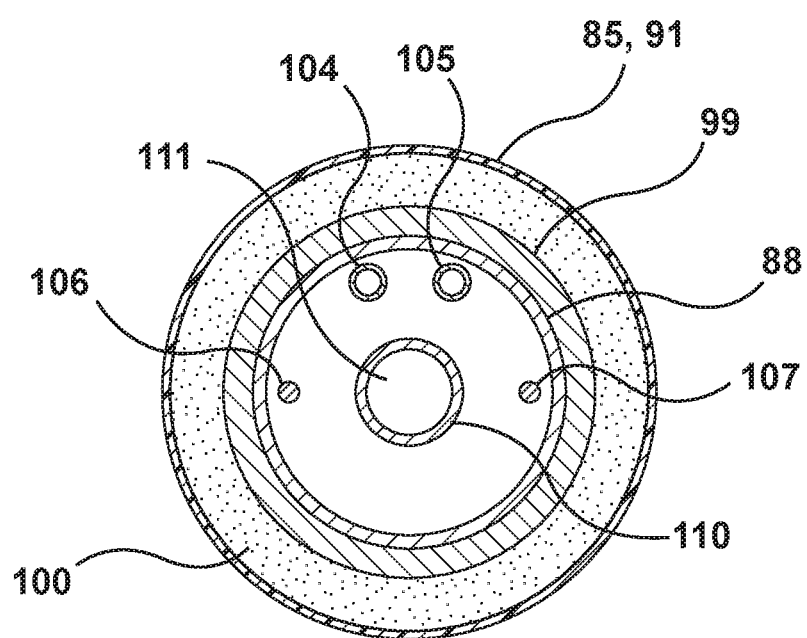
FIG. 6B is a cross sectional view of FIG. 6A.

Alternatively, as shown in FIGS. 5, 6A and 6B, RF electrode 99 may have a longer length 98 than electrode 86 (e.g., in a range of 2 to 15 mm) if it is made to be flexible. For example, a flexible RF electrode may be a wire 99 coiled around the shaft 88 or may be flexible wire filaments. RF electrodes that are flexible and approximately the same length as the ablation element's active ablation length 92 of an expected ablation zone 49 (shown in FIG. 1) may in particular be radiopaque and indicate a position of the ablation element in the body accurately. In some embodiments, the length of the electrode is from 120% to 75% of the length of the active ablation length of the ablation element. In FIG. 5, the length of the electrode is about the same as the length of the active ablation length (i.e., 100% of the length). Optionally, a fluid delivery port 87 may be positioned on the shaft 88 under a flexible RF electrode (e.g., wire coil electrode 99) and the flexible electrode may have sufficient space between wires or revolutions of a coil to allow conductive fluid 100 to easily flow. For example, in side view such as in FIG. 5, the fluid delivery port is apparent between the windings of the electrode. Alternatively, one or more fluid delivery ports may be positioned on the shaft 88 axially next to an RF electrode 99, for example distal to the electrode as shown in FIG. 6A and an optional fluid return port 97 may be positioned on the shaft 88 proximal to the electrode. The fluid delivery port may be an opening in an infusion lumen 104 that runs the length of the catheter to a proximal region where it is connectable to a fluid source. Optionally the infusion lumen 104 may be a lumen in an elongate tube (e.g., polyimide or the like) positioned within a lumen of the shaft 88. The fluid return port may be an opening in a drain lumen 105 that runs the length of the catheter to a proximal region where it may be connectable to a fluid disposal container. Optionally the drain lumen 105 may be a lumen in an elongate tube (e.g., polyimide or the like) positioned within a lumen of the shaft 88.

A temperature sensor 95 (e.g., T-Type thermocouple) may be positioned within the cavity defined by the membrane 85 and optionally connected to the RF electrode. The temperature sensor 95 may be a thermocouple that is a junction of thermocouple wires 106 that run the length of the catheter to the proximal end of the catheter where it is connectable to a console or thermometer. The electrode (for example, electrodes 86 or 99) is connected to an RF wire 107 that is connectable to a console or RF source at the catheter's proximal region. The optional proximal stimulation electrode 101 and optional distal stimulation electrode 102 are connected to a proximal stimulation wire 108 and distal stimulation wire 109 respectively that are connectable to a console or stimulation generator at the catheter's proximal region. The console (not shown) may deliver a stimulation waveform to the proximal stimulation electrode 101 and distal stimulation electrode 102 via the proximal and distal stimulation wires 108, 109 in a bipolar configuration to identify proximity to a target nerve (e.g., GSN) or confirm ablation, examples of which are described herein, as well as incorporated by reference from U.S. Pub. No. 2018/0110561 and PCT Pub. No. WO2018/023132. The console may deliver RF energy to the electrode (e.g., electrodes) 86, 99 via the RF wire 107 and complete the RF circuit with a dispersive ground pad positioned on the patient's skin or an alternative return electrode positioned on the catheter 81 or delivery sheath.

The ablation element 91, in a deployed or expanded configuration (e.g., FIG. 1), may be approximately cylindrical in shape with tapered or rounded ends 93, 94 (shown in FIG. 1) and may have an active ablation length 92 in a range of 5 to 20 mm. In some embodiments the active ablation length 92 may be in a range of 10 to 20 mm (e.g., 12 to 16 mm), which may generate an ablation lesion having a length similar to the active ablation length which is capable of covering the entire target region 58 where the target nerve (e.g., GSN 52, GSN root 53, TSN 51) is expected to reside and where non-target nerves (e.g., sympathetic trunk 54—see FIG. 1) are not expected to reside. An advantage of ablation elements that have these active ablation lengths is that the ablation element can be used to effectively deliver one single ablation that is expected to ablate the target nerve in a large majority of patients. An advantage of this one-shot approach is that a single ablation episode (e.g., RF energy on to RF energy off) can be used to perform the treatment. This is in contrast to some methods that must move an ablation device within a vessel in between ablation episodes, which can take much longer to complete. If a target nerve is missed following ablation in a first target vein (e.g., T11 intercostal vein), or the first target vein is not suitable for catheter placement, the medical device may be moved to a second target vein (e.g., an adjacent intercostal vein, e.g., a T10 intercostal vein) and another ablation episode may be performed in the target region of the second target vein. The target region for the ablation element within the second vein can be the same as the first vein.

In alternative embodiments the active ablation length 92 may be in a range of 5 to 10 mm, which may be shorter than the entire target region within the target vein. In some exemplary methods, in order to ensure efficacious ablation of a target nerve, multiple ablations may be required to cover the entire target region 58 and also create a lesion that will likely include the target nerve. Alternatively, nerve stimulation may be performed by delivering a nerve stimulation signal from optional stimulation electrodes (e.g., electrodes 101, 102) prior to ablation to confirm, for example, that ablation element is in a proper position near the target nerve, and optionally during or following ablation to confirm if the nerve has been deactivated. If the nerve has been deactivated (which may be detected from a nerve stimulation process), a subsequent ablation does not need to be performed. If it is detected that the nerve has not been destroyed, the ablation element may be repositioned to a second location within the same target region of the same target vein to and a second ablation episode can then occur.

Membrane 85 may be a microporous membrane having pores passing through the membrane that have diameters in the range of 100 to 150 picometers (i.e., 0.1 to 0.15 nanometers), which are small enough to disallow water molecules that have a size of about 290 pm or chloride ions that have a size of about 180 pm from passing through, yet large enough to allow sodium ions that have a size of about 100 pm to pass through. In use, the RF electrical current passes through the microporous membrane to generate an electromagnetic field in tissue around the ablation electrode with a current density sufficient to heat the tissue to coagulation and ablative temperatures (e.g., tissue temperature in a range of 60 to 99 degrees C.). Materials and methods of manufacturing microporous membrane as well as physics of conducting RF from conductive fluid (e.g., hypertonic saline) through a microporous membrane are known in the art and therefore are not repeated herein. For example, the descriptions of U.S. Pat. Nos. 5,797,903 and 5,846,239 are fully incorporated by reference herein, to the extent that they are applicable. Hypertonic saline may be delivered to the cavity within the ablation element with a low pressure (e.g., less than 2 atm). Benefits of an ablation element comprising a membrane as its outer surface include flexibility and ability to bend, which can be desired when traversing a vascular bend, and in particular for an ablation element having a length of, e.g., 10 to 20 mm that needs to be delivered over a bend radius in a range of 4 to 15 mm, as is the case from an azygos vein to an intercostal vein. The membrane can optionally fold to achieve a smaller diameter during delivery and be deployed to achieve a larger diameter once positioned in a target region of a target vein. Additionally, the membrane can allow the ablation element to be compressed when external pressure is greater than internal pressure (e.g., when advancing into a vein having a smaller lumen diameter than the maximum outer diameter of the ablation element) to achieve a tight fit in varying vessel sizes or shapes. A membrane can also allow the ablation element to be expanded when internal pressure is greater than external pressure (e.g., when conductive fluid within the cavity of the ablation element is pressurized) which can allow delivery of the ablation element in a state having a smaller diameter than the target vessel and expansion of the ablation element once positioned to facilitate delivery, and achieve a tight fit in varying vessel sizes or shapes wherein a tight fit provides excellent contact between the membrane and tissue allowing consistent and controllable RF energy delivery.

Alternatively, a membrane (e.g., membrane 85) may be an electrically conductive polymer. For example, the electrically conductive polymer may be made with a polymer comprising electrically conductive filaments or an ionomer such as Nafion®. Nafion membranes conduct cations, such as Na+. They absorb water, but do not allow water to flow through in a liquid state. The size of pores, called domains, in a Nafion membrane are small before the membrane absorbs water. As water is absorbed the pore size increases allowing the Na+ transfer through the membrane. Nafion membrane electrical conductivity increases with temperature as long as the membrane is kept wet. Other general materials and basic methods of manufacturing electrically conductive membranes as well as basic physics of conducting RF from hypertonic saline through an electrically conductive membrane are known in the art and therefore are not repeated herein.

Alternatively, any membrane herein may be configured to generate an electromagnetic field in surrounding tissue via capacitive coupling across the membrane. Materials and methods of manufacturing capacitive coupling membranes as well as physics of capacitive coupling RF from hypertonic saline through a membrane are known in the art, and basic and known concepts thereof are fully incorporated by reference herein.

Alternatively, any membrane herein may be a weeping membrane, for example the membrane may comprise pores large enough to allow liquid hypertonic saline to pass through and carry an electrical current. Materials and methods of manufacturing weeping membranes as well as physics of conducting RF from hypertonic saline through a weeping membrane are known in the art and therefore are not repeated herein.

Alternatively, any membrane herein may be impregnated or have a coating that may function to improve deliverability or deployability, reduce stickiness, or facilitate removal from a vein. Examples of materials that may be used to coat or impregnate membranes include non-alcohol stable and biocompatible hydrophilic chemicals such as hyaluronic acid.

Any membrane herein, regardless of the specific mode of energy transfer to the target tissue (e.g., weeping, capacitive coupling) can have any of the suitable features or properties of any of the membranes described herein, including active ablation length, shape when expanded (e.g., cylindrical), etc.

Figure 2:
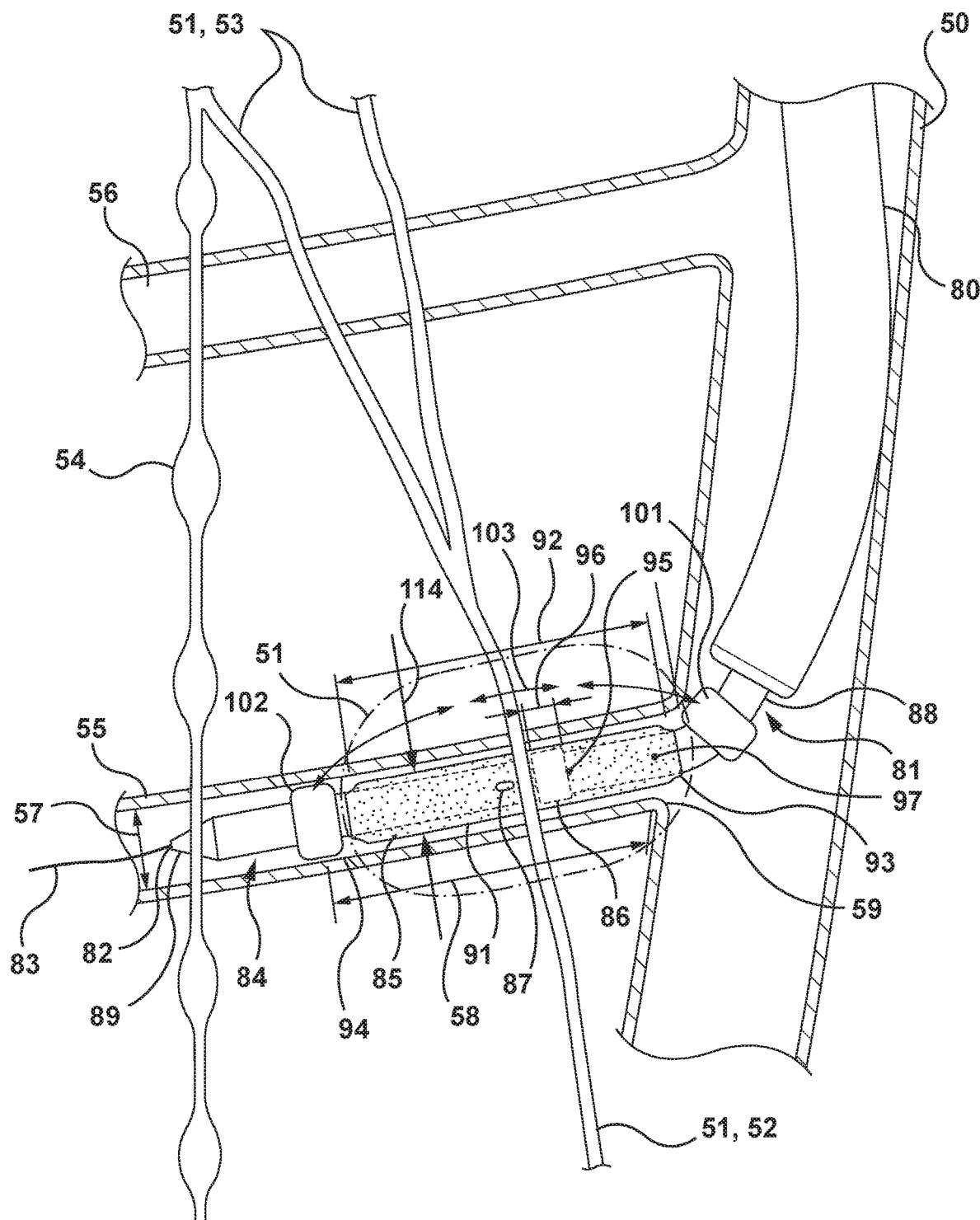
FIG. 2 is a schematic illustration of an ablation catheter with an ablative membrane electrode in an undeployed state positioned in an intercostal vein.
Figure 3C:
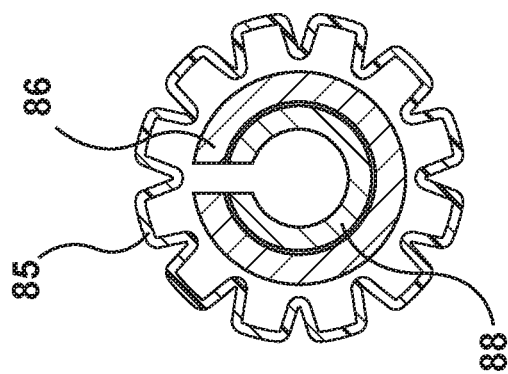
FIGS. 3A, 3B and 3C are cross sectional views of deployable membrane electrodes in undeployed states.
Figure 3B:
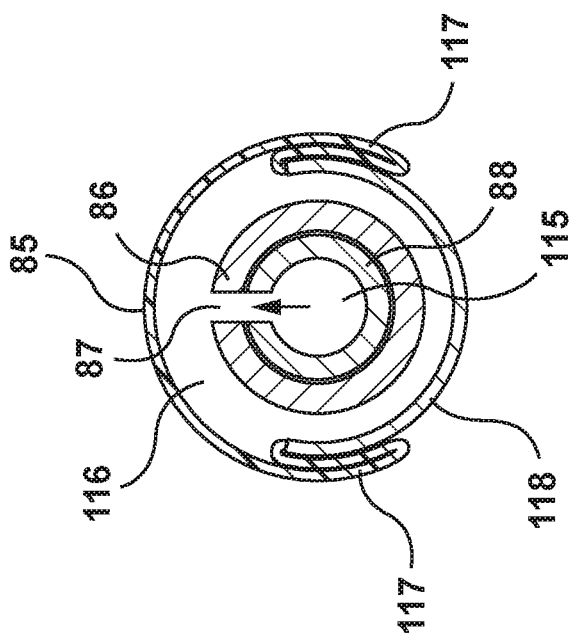
Figure 3A:
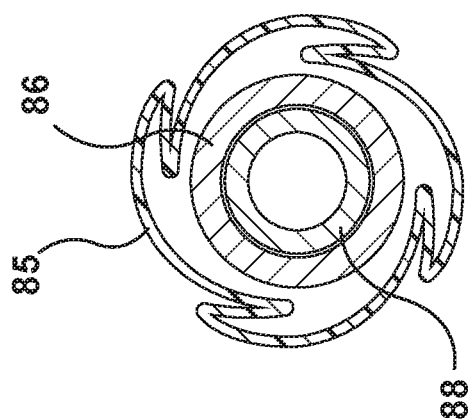

In some embodiments an ablation element (e.g., element 91) is configurable in at least one delivery state and in at least one deployed state, wherein in the delivery state the ablation element is radially more contracted than in the deployed state. For example, the ablation element 91 may have a maximum outer diameter 114 in the delivery state (as shown in FIG. 2) in a range of 1.5 to 2.5 mm and a maximum outer diameter 90 in the deployed state (as shown in FIG. 1 in a range of 2 to 4 mm. The length of the ablation element may be in a range of 5 to 20 mm and be the same for both the delivery and deployed states. The volume of the cavity containing hypertonic saline when the ablation element is in a deployed state may be in a range of 15 to 252 $mm^3$. The ablation element may be transitioned from the delivery state to the deployed state by injecting conductive fluid into the cavity surrounded by the membrane 85 to increase fluid pressure in the cavity to expand the membrane. The membrane optionally is made with folds that allow it to obtain the contracted delivery state and unfold when pressurized into the deployed state. The folds may further facilitate collapsing the membrane from an expanded deployed state to a contracted delivery state. Optionally, the ablation element may be transitioned from the deployed state to the delivery state by reducing pressure in the cavity for example by extracting fluid from the cavity or applying a vacuum. For example, FIGS. 3A, 3B, and 3C show cross sectional illustrations of a shaft 88 having a fluid delivery lumen 115, which may contain a guidewire tube (not shown). Around the shaft 88 is an electrode 86. A fluid delivery port 87 may pass from the fluid delivery lumen through the shaft 88 and optionally through the electrode 86 to a chamber or cavity 116 defined by the membrane 85. The membrane 85 may have longitudinal pleats or folds 117 that facilitate transition from an undeployed to deployed state and back again. This description can apply to any of the membranes and medical devices herein.

In alternative embodiments a device may have an ablation element that in use has a consistent maximum outer diameter 90 that is within 0.5 mm, equal to, or greater than by up to 1.5 mm the diameter 57 of the target vessel during delivery into the target vessel. The distal tip 89 of the device 81 may be tapered (as shown in FIG. 1) to facilitate advancement into a narrow vein. Optionally, a device may further comprise a distal shaft section 110 positioned distal to the optional distal stimulation electrode 102 that has greater flexibility than the shaft 88, as shown in FIG. 4. The tapered end 89 may be particularly valuable to get the distal tip into the vein and if necessary, to distend the vessel as it is advanced through it. Such a device may be particularly suitable when a target region for placement within the vein is within a short distance (e.g., within 20 mm) of the entrance to a target vein from a larger vein (e.g., within 20 mm from the ostium of an azygous vein/intercostal vein), or when a target region for placement within a vein is within a distance of the entrance to a target vein from a larger vein that is similar (e.g., within 5 mm) to a length of the ablation element. In other words, it may be quite difficult without a tapered region to deliver such a sized ablation element much deeper into a vessel that has a lumen similar or smaller than the ablation element. For example, as shown in FIG. 1, exemplary ablation element 91 has a maximum outer diameter 90 when expanded (e.g., in a range of 2 mm to 4 mm) and an active ablation length 92 (e.g., in a range of 5 to 20 mm) and in use can be delivered from an azygos vein 50 having a lumen diameter larger than the outer diameter 90, into an intercostal vein 55 having a lumen diameter 57 that is similar or smaller than the outer diameter 90, and the ablation element 91 is positioned in a target region 58 in the intercostal vein 55 that begins at the entrance or ostium 59 of the intercostal vein and has a length similar to the active ablation length 92. For example, a volume of a cavity defined by the membrane of an ablation element having a consistent diameter may be in a range of about 15 mm3 to 252 mm3.

Optionally, as shown in FIG. 1 a temperature sensor 95 is positioned within the cavity for example in contact with the RF electrode 86 for monitoring temperature of the conductive fluid or the RF electrode 86. For example, the temperature sensor 95 may be a T-type thermocouple and can be electrically connected to a proximal end of the catheter via a copper and constantan wire pair, which is at the proximal end of the catheter connectable to a computer-controlled energy delivery console. An energy delivery algorithm may detect the temperature in the cavity and deliver RF energy as a function of the temperature for example to avoid over heating or boiling the conductive fluid. Optionally, an external temperature sensor (not shown) may be located external to the membrane for example on the membrane's exterior surface or on the catheter shaft 88 proximate to the ablation element 91. The external temperature sensor may indicate tissue or blood temperature more accurately than the internal temperature sensor 95.

Optionally, any of the catheters herein may further comprise one or more nerve stimulation electrodes positioned near the ablation element 91. Preferably (if stimulation electrodes are included) as shown in FIG. 1, a proximal nerve stimulation electrode 101 is positioned proximal of the ablation element 91 and within 5 mm (e.g., within 2 mm, within 1 mm) of the proximal end 93 of the ablation element, and a distal nerve stimulation electrode 102 is positioned distal of the ablation element 91 and within 5 mm (e.g., within 2 mm, within 1 mm) of the proximal end 93 of the ablation element. Preferably, the proximal nerve stimulation electrode 101 and distal nerve stimulation electrode 102 are separated by a distance of no more than 25 mm (e.g., no more than 20 mm) and the ablation element is positioned between them. Optional nerve stimulation electrodes 101 and 102 may be made from an electrically conductive material such as stainless steel and may be band electrodes wrapped around the catheter shaft 88 and have a length in a range of 1 to 2 mm. Optionally, the nerve stimulation electrodes may contain radiopaque material such as platinum iridium. Optionally, the electrodes 101 and 102 may be used to crimp the membrane (e.g., membrane 85) to the shaft 88. Each nerve stimulation electrode is electrically connected via independent conductors (not shown) travelling through the catheter to the proximal end of the catheter where they are connectable to a nerve stimulation signal supply, which may also be a computer-controlled RF ablation energy console. In use the nerve stimulation electrodes 101 and 102 may be positioned at a proximal and distal end of a target region 58 of a target vessel 55, 56, which can be visualized for example with fluoroscopy by placing the proximal electrode 101 at the ostium 59 of the target vessel 55 as shown in FIG. 1. The nerve stimulation electrodes 101 and 102 may deliver a nerve stimulation signal 103 in bipolar mode concentrating the signal between the two electrodes to generate an action potential of a nerve positioned between them and also within an ablation zone of the ablation element 91. The distance between the two nerve stimulation electrodes 101 and 102 of no more than 25 mm ensures a pacing vector having a nerve stimulation signal strength capable of stimulating a nerve within the vector. Nerve stimulation (i.e., pacing) parameters may include 50 Hz and 1V used to generate an action potential of a TSN or GSN. Stimulation of a TSN or GSN may result in a measurable physiological response for example an epigastric response such as contraction of the rectus abdominis muscle, increased heart rate, or increased blood pressure. A positive stimulation of a TSN or GSN can confirm the ablation element is in an appropriate location within the vessel to ablate the targeted TSN or GSN while lack of response can suggest the ablation element needs to be moved. Nerve stimulation parameters may include 2 Hz and 2V used to stimulate intercostal nerves or the sympathetic trunk to confirm clearance from intercostal nerves when a lack of intercostal muscle response is measured or to confirm clearance from the sympathetic trunk when a lack of response from sympathetic trunk is measured. The electrodes 101 and 102 may optionally or alternatively be used to measure bioimpedance and phase of tissue in the pacing range 103 which can be used to detect presence of nerve tissue, detect tissue changes caused by ablation, detect abrupt impedance changes which may be predictive of ensuing safety concerns (e.g. blood coagulation, overheating, bubble formation). Optionally, a nerve stimulation signal may have features that reduce or eliminate stimulation of pain fibers and yet stimulate a target TSN or GSN.

Optionally or alternatively, a nerve stimulation electrode may be positioned on an external surface of the membrane.

In some embodiments such as the device shown in FIG. 1, the ablation element 91 has a membrane 85 around its circumference and is capable of delivering ablative energy to the target region 58 of the target vessel 55 circumferentially, in other words in a radially symmetric pattern. A benefit of this feature may be that a user does not need to consider radial orientation or torque the catheter to adjust radial orientation, which may reduce procedure time or user error. However, in alternative embodiments an ablation element may direct ablation energy toward a segment of the circumference, for example the segment may be less than or equal to 50% of the circumference (e.g., less than 40%, less than 30%, less than 25%). A directional ablation catheter may direct ablation energy toward a target nerve, which may require less ablation energy, reduce a risk of injuring non-target tissue, reduce pain, or reduce injury or shrinkage of the target vessel. When used to ablate a TSN or GSN from an intercostal vein, the TSN or GSN is always in the same direction relative to the vein, which is away from the vertebra and toward the lung. In some examples (not shown), a radiopaque marker of the catheter may be used to facilitate radial orientation of the catheter. The desired orientation may be the orientation in which the directed ablation energy will be aimed in a radial direction that is away from the vertebra (e.g., opposite the vertebra) and towards the lung. For example, if the target vessel is a right T11 intercostal vein, a C-arm fluoroscope may be centered on a T11 vertebra, and optionally rotated from an anterior-posterior center position (AP position) to the patient's right side to obtain an angle that is approximately orthogonal to the tangent of the vertebra. In this position, it can be desired to have the directed ablation energy aimed in a radial direction toward the C-arm head, which is where the TSN often traverses intercostal veins. The catheter may be torqued to rotate the catheter distal section 84 within the intercostal vein until the radiopaque marker indicates that the ablation energy will be aimed toward the C-arm and thus toward the target nerve. The radiopaque marker may be configured to distinguish when the radiopaque marker is rotationally aimed at a C-arm head. Since the position of the radiopaque marker is circumferentially aligned with the direction of ablation, the radiopaque marker can be used to indicate when the direction of ablation is aimed at a C-arm head. The radiopaque marker is made from a radiopaque material and is asymmetric in shape. For example, the radiopaque marker may be N-shaped. If the radiopaque marker is facing towards the C-arm head, the radiopaque marker will appear as the letter N. If the radiopaque marker is facing away from the C-arm head (e.g., toward the vertebra), the radiopaque marker will appear as a backwards letter N. If the radiopaque marker is sideways in relation to the C-arm, the radiopaque marker will appear as a line. Optionally, a device may further include an additional radiopaque marker that is configured to visually indicate when the rotational position of the catheter's distal section 84 is within a set tolerance. Particularly, the additional radiopaque marker can include two lines the center of which is circumferentially spaced from the first radiopaque marker by about 180 degrees, so that the first radiopaque marker appears between the lines of the additional radiopaque marker when the orientation is within the set tolerance. When the orientation is outside the set tolerance, the radiopaque marker will overlap one of the lines of the additional radiopaque marker or will be outside of the lines of the additional radiopaque marker. For example, the set tolerance may be up to 45 degrees on either side of perfect alignment (e.g. up to 35 degrees, or 25 degrees, or 15 degrees, or 5 degrees).

An ablation element having a membrane (e.g., microporous membrane, semipermeable membrane, conductive membrane, weeping membrane) may be configured for directional energy delivery by having the membrane only on the energy delivery segment of the circumference and the remainder of the circumference may be an electrically resistive material. FIG. 3B shows a cross section of an ablation section of a catheter wherein the membrane 85 (e.g., microporous membrane, semipermeable membrane, conductive membrane, weeping membrane) surrounds a portion of the circumference while the remainder of the circumference 118 is made from a non-conductive material. The region 118 may extend around any desired portion of the circumference, such as no more than 50%, no more than 45%, etc.

In some embodiments of a GSN ablation procedure herein, the lowest intercostal vein is first targeted because in a majority of patients a fully formed GSN traverses the lowest intercostal vein within the target region that is between the adjoining azygos vein and to a distance up to 20 mm into the intercostal vein from the ostium. However, in some patients where a first ablation is not sufficient, a test may be done to assess a clinical effect and subsequent ablations of target regions at one or two additional levels may be done to achieve a clinically significant effect. For example, the following description is an exemplary method of treating heart failure in a human patient by ablating a thoracic splanchnic nerve. A distal region of an ablation catheter comprising an ablation element can be delivered to a first intercostal vein (e.g., the lowest intercostal vein, a T11 intercostal vein) of the patient. Ablation energy can then be delivered from the ablation catheter to create a first lesion (e.g., a lesion having a length in a range of 10 to 20 mm, e.g., in a range of 12 to 15 mm) in tissue up to 5 mm from the first intercostal vein. The distal region of the ablation catheter can be moved to a second intercostal vein that is superior to (e.g., superior to and adjacent to) the first intercostal vein. An ablation confirmation test can then be performed. Monitoring can be performed for a physiological response (e.g., splanchnic vasoconstriction, increased heart rate, increased blood pressure) to the ablation confirmation test. If the physiological response demonstrates that the first lesion did not provide a clinically significant amount of GSN blocking (e.g., by observing a lack of physiological response) then ablation energy can be delivered from the ablation catheter to create a second lesion in tissue up to 5 mm from the second intercostal vein. The distal region of the ablation catheter can be moved to a third intercostal vein that is superior to (e.g., superior and adjacent to) the second intercostal vein. The same or different ablation confirmation test can be performed, followed by another monitoring test. If the physiological response demonstrates that the first lesion and second lesion did not provide a clinically significant amount of GSN blocking (e.g., by observing a lack of physiological response) then ablation energy can be delivered from the ablation catheter to create a third lesion in tissue up to 5 mm from the third intercostal vein. Any of the the ablation confirmation tests may comprise delivering a nerve stimulation signal from a stimulation electrode positioned on the distal region of the ablation catheter configured to generate an action potential in the thoracic splanchnic nerve. Alternatively or in addition to, the ablation confirmation test may comprise a leg raise test. Alternatively or in addition to, the ablation confirmation test may comprise adding fluid volume to the venous system. Alternatively or in addition to, the ablation confirmation test may comprise a hand-grip test.

In exemplary methods in which an ablation confirmation test includes a leg raise test, the method may comprise any of the following steps. Prior to ablation in the lowest intercostal vein, a baseline measurement may be obtained by raising the legs and measuring the change in central venous pressure and waiting for equilibration, that is a measure of the total venous compliance including the central veins and splanchnic bed. The legs can then be lowered, to allow equilibration so blood redistributes back to the legs. An ablation in the lowest intercostal vein (e.g. T11) can then be performed as set forth herein. The legs can then be raised, followed by waiting for equilibration and re-measure central venous pressure. A measurement can then be made to determine if there was an appropriate reduction in total venous compliance. If yes, then the GSN has successfully been ablated. If no, then an ablation in the next higher intercostal vein (e.g., T10) can be performed, as set forth herein. The measurement can be repeated. A determination can then be made to see if there was an appropriate reduction in total venous compliance. If yes, then the GSN has successfully been ablated. If no, then an ablation in the next higher intercostal vein (e.g., T9) can be performed.

In exemplary methods in which an ablation confirmation test comprises a hand-grip or other activity that increases sympathetic nervous system (SNS) outflow to the splanchnic bed may comprise the following steps. An ablation can be performed in a lowest intercostal vein (e.g., T11). Venous compliance can then be measured. A hand-grip can then be performed for a predetermined amount of time (e.g., 60 seconds). Venous compliance can then be remeasured. If there is no change in venous compliance, the initial ablation was sufficient to achieve a clinically significant outcome. If there still is a decrease in compliance, some of the SNS activity caused by the hand-grip is getting through. The ablation in the lowest intercostal vein was thus insufficient to achieve a clinically significant effect. An ablation in the next higher intercostal vein (e.g., T10) can then be performed. A hand grip test for a predetermined amount of time (e.g., 60 seconds) can be performed. Venous compliance can then be remeasured. If there is no change in compliance, the second ablation was sufficient. If there is a decrease in compliance, some of the SNS activity caused by the hand-grip is getting through, and the ablation in the next higher intercostal vein was thus insufficient to achieve a clinically significant effect. Ablation is the next higher intercostal vein (T9) can then be performed. The procedure is done at this point as ablation at a level higher than the 3rd lowest intercostal vein is not anticipated.

In any of the methods herein, including ablation confirmation tests herein, not all of the steps need necessarily to be performed. And some of the steps may occur in different orders. It is of note that the procedures herein are intending to target particular nerves or nerve roots, and are doing so from particular target veins, and even within those veins are placing ablation elements or members within certain regions. The anatomical regions that are being accessed and targeted necessitate certain design requirements. In other treatments that are targeting different anatomical locations for placement, and targeting different target nerves, the device design constraints for those approaches are very different, and thus the devices that can be used in those treatments may be very different. The disclosure herein thus provides specific reasons for designing particular devices, and those reasons include being able to effectively carry out the treatments specifically set forth herein.

While the above description provides examples of one or more processes or apparatuses, it will be appreciated that other processes or apparatuses may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

Specific embodiments described herein are not intended to limit any claim and any claim may cover processes or apparatuses that differ from those described below, unless specifically indicated otherwise. The claims are not limited to apparatuses or processes having all of the features of any one apparatus or process described below or to features common to multiple or all of the apparatuses described below, unless specifically indicated otherwise. It is possible that an apparatus or process described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

What is claimed is:

1. A method of ablating a greater splanchnic nerve or a greater splanchnic nerve root to increase splanchnic venous blood capacitance, comprising:
    advancing an elongate medical device into an azygos vein, the elongate medical device including a distal region and an ablation element disposed at the distal region;
    advancing the ablation element from the azygos vein into a T9, T10, or T11 intercostal vein;
    when the ablation element is disposed in the T9, T10, or T11 intercostal vein, delivering energy from the ablation element; and
    creating a lesion having a length in a range of 5 to 20 mm, whereby creating the lesion ablates a portion of the greater splanchnic nerve or the greater splanchnic nerve root.

2. The method of claim 1, wherein the elongate medical device comprises a fluid lumen and the distal region includes an inflatable membrane, the method further comprising delivering a fluid through the fluid lumen and into inflatable membrane to thereby inflate the inflatable membrane to an expanded configuration.

3. The method of claim 1, wherein creating the lesion having a length in a range of 5 to 20 mm comprises creating a continuous circumferential lesion having a length in a range of 5 to 20 mm.

4. The method of claim 1, wherein creating the lesion comprises creating a lesion that has a depth of at least 5 mm.

5. The method of claim 1, wherein advancing the ablation element from the azygos vein into the T9, T10, or T11 intercostal vein comprises maintaining a position of the ablation element from an ostium of the azygos vein to the intercostal vein to up to 20 mm from the ostium.

6. The method of claim 1, wherein advancing the ablation element from the azygos vein into the T9, T10, or T11 intercostal vein comprises maintaining a position of the ablation element from an ostium of the azygos vein to the intercostal vein to up to 15 mm from the ostium.

7. The method of claim 1, wherein advancing the ablation element from the azygos vein into the T9, T10, or T11 intercostal vein comprises advancing the ablation element from the azygous vein into the T11 intercostal vein.

8. The method of claim 7, further comprising performing an ablation confirmation test, and repositioning the ablation element into the T10 intercostal vein and delivering energy from the ablation element.

9. The method of claim 7, further comprising performing an ablation confirmation test, and repositioning the ablation element into the T9 intercostal vein and delivering energy from the ablation element.

10. The method of claim 1, further comprising, prior to delivering the energy, delivering stimulation energy to first and second stimulation electrodes carried by the medical device to determine if the ablation element is in a target location within the intercostal vein.

11. The method of claim 1, wherein delivering energy comprises delivering energy from less than 100% of a circumference of the ablation element.

12. The method of claim 11, wherein delivering energy comprises delivering energy from less than 50% of the circumference of the ablation element.

* * * * *